(12) United States Patent
Chen et al.

(10) Patent No.: US 9,480,479 B2
(45) Date of Patent: Nov. 1, 2016

(54) VASO-OCCLUSIVE DEVICE DELIVERY SYSTEM

(71) Applicants: STRYKER CORPORATION, Kalamazoo, MI (US); STRYKER NV OPERATIONS LIMITED, Dublin (IE)

(72) Inventors: Hancun Chen, San Ramon, CA (US); Richard Murphy, Sunnyvale, CA (US); Jimmy Dao, San Jose, CA (US); Justin Vo, San Jose, CA (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 207 days.

(21) Appl. No.: 14/457,970

(22) Filed: Aug. 12, 2014

(65) Prior Publication Data

US 2015/0057700 A1    Feb. 26, 2015

Related U.S. Application Data

(60) Provisional application No. 61/867,957, filed on Aug. 20, 2013, provisional application No. 61/897,151, filed on Oct. 29, 2013.

(51) Int. Cl.
*A61B 17/12* (2006.01)
*A61B 17/00* (2006.01)

(52) U.S. Cl.
CPC ..... *A61B 17/12113* (2013.01); *A61B 17/1214* (2013.01); *A61B 17/12109* (2013.01);
(Continued)

(58) Field of Classification Search
CPC .......... A61B 17/12113; A61B 17/12145; A61B 17/1214; A61B 17/12109; A61B 17/12154; A61B 17/1215; A61B 17/12172; A61B 2017/12054; A61B 2017/12059; A61B 2017/12063; A61B 2017/12068; A61B 2017/12072; A61B 2017/12077; A61B 2017/1209; A61B 2017/00199; A61B 2017/1205

See application file for complete search history.

(56) References Cited

U.S. PATENT DOCUMENTS

| 4,994,069 | A  | 2/1991 | Ritchart et al. |
| 5,984,929 | A  | 11/1999 | Bashiri et al. |
| 8,202,292 | B2 | 6/2012 | Kellett |
| 2007/0055302 | A1 | 3/2007 | Henry et al. |

(Continued)

FOREIGN PATENT DOCUMENTS

EP    0992220 A1    4/2000

OTHER PUBLICATIONS

PCT Notification of Transmittal of International Search Report and Written Opinion for International Application No. PCT/US2014/050755, filed Aug. 12, 2014, Applicant Stryker Corporation, forms PCT/ISA/220, 210 and 237, mailed Dec. 19, 2014 (16 pages).

(Continued)

*Primary Examiner* — Jocelin Tanner
(74) *Attorney, Agent, or Firm* — Vista IP Law Group, LLP

(57) ABSTRACT

A vaso-occlusive delivery system includes a vaso-occlusive coil, delivery wire assembly, and a link. The vaso-occlusive coil defines a coil lumen and has first and second coil windings defining a coil opening therebetween. The delivery wire assembly defines a delivery wire lumen, and includes an electrolytic detachment zone, a delivery wire conduit, and a delivery wire attached to the delivery wire conduit and extending through the delivery wire lumen distal of the delivery wire conduit. The link defines a link lumen and has link body including a proximal end of the link body defines an link opening in communication with the link lumen and a distal end of the link body includes a link detent extending radially from the link body, through the coil opening, securing the link body and the delivery wire assembly to the vaso-occlusive coil.

13 Claims, 16 Drawing Sheets

(52) U.S. Cl.
CPC ...... *A61B17/12145* (2013.01); *A61B 17/1215* (2013.01); *A61B 17/12154* (2013.01); *A61B 2017/00199* (2013.01); *A61B 2017/1205* (2013.01); *A61B 2017/12054* (2013.01); *A61B 2017/12063* (2013.01); *A61B 2017/12068* (2013.01); *A61B 2090/3966* (2016.02)

(56) References Cited

U.S. PATENT DOCUMENTS

2007/0293928 A1* 12/2007 Tomlin ............. A61B 17/12022
623/1.11
2009/0177261 A1 7/2009 Teoh et al.
2010/0160944 A1 6/2010 Teoh et al.

OTHER PUBLICATIONS

PCT Invitation to Pay Additional Fees for International Application No. PCT/US2014/050755, application Stryker Corporation, mailed on Nov. 6, 2014 (5 pages).

U.S. Appl. No. 14/206,244, entitled "Vaso-Occlusive Device Delivery System", filed Mar. 12, 2014, inventors Lantao Guo et al., specification and drawings (24 pages).

* cited by examiner

VASO-OCCLUSIVE DEVICE DELIVERY SYSTEM

RELATED APPLICATIONS DATA

The present application claims the benefit under 35 U.S.C. §119 to U.S. Provisional Application Ser. Nos. 61/867,957, filed Aug. 20, 2013, and 61/897,151, filed Oct. 29, 2013. The foregoing applications are hereby incorporated by reference into the present application in their entirety.

FIELD

The field of the disclosed inventions generally relates to systems and delivery devices for implanting vaso-occlusive devices for establishing an embolus or vascular occlusion in a vessel of a human or veterinary patient. More particularly, the disclosed inventions relate to securing a vaso-occlusive coil to a pusher assembly.

BACKGROUND

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference as though set forth in full, describes a vaso-occlusive device that assumes a linear, helical primary shape when stretched for placement through the lumen of a delivery catheter, and a folded, convoluted secondary shape when released from the delivery catheter and deposited in the vasculature.

In order to deliver the vaso-occlusive devices to a desired site in the vasculature, e.g., within an aneurysmal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysm once the guidewire is withdrawn. A delivery or "pusher" assembly is then passed through the micro-catheter, until a vaso-occlusive device secured to a distal end of the pusher assembly is extended out of the distal end opening of the micro-catheter and into the aneurysm. The proximal end of the vaso-occlusive device is typically secured to the distal end of the pusher assembly with an adhesive at what is known as a "major junction" of the vaso-occlusive device delivery assembly.

Another vaso-occlusive device delivery assembly major junction design is disclosed in U.S. Pat. No. 8,202,292, issued to Kellett, which is fully incorporated herein by reference as though set forth in full. The major junction includes a flat adapter connecting a delivery wire to a vaso-occlusive coil. The delivery wire has a hook or "J" shape distal end configured to be received in an aperture in the proximal end of the adapter to attach the delivery wire to adapter. The vaso-occlusive coil has windings that define openings configured to receive fingers in the distal end of the adapter to attach the vaso-occlusive coil to the adapter. Consequently, the adapter facilitates attachment of the delivery wire to the vaso-occlusive coil.

Once in the aneurysm, segments of some vaso-occlusive devices break off to allow more efficient and complete packing. The vaso-occlusive device is then released or "detached" from the end of the pusher assembly, typically by detaching a distal end of the pusher assembly. Then the pusher assembly is withdrawn back through the catheter. Depending on the particular needs of the patient, one or more additional occlusive devices may be pushed through the catheter and released at the same site.

One well-known way to release a vaso-occlusive device from the end of the pusher assembly is through the use of an electrolytically severable junction, which is a small exposed section or detachment zone located along a distal end portion of the pusher assembly. The detachment zone is typically made of stainless steel and is located just proximal of the vaso-occlusive device. An electrolytically severable junction is susceptible to electrolysis and disintegrates when the pusher assembly is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher completes an electrolytic detachment circuit with a return electrode, and the detachment zone disintegrates due to electrolysis. Other detachment mechanisms for releasing a vaso-occlusive device from a pusher assembly include mechanical, thermal, and hydraulic mechanisms.

While major junctions secured with an adhesive and those including a flat adapter have performed well, connections between the delivery wire, the vaso-occlusive coil, and the adapter can be improved. Accordingly, there remains a need for other systems and methods for securing a vaso-occlusive device to a pusher assembly at a major junction.

SUMMARY

In one embodiment of the disclosed inventions, a vaso-occlusive device delivery assembly includes a pusher assembly, an elongate tubular member, a vaso-occlusive coil, and a locking pin. The pusher assembly defines a longitudinal axis. The elongate tubular member is attached to, and extends distally from, a distal end of the pusher assembly. The tubular member is aligned with the longitudinal axis of the pusher assembly and has a tubular member wall. The vaso-occlusive coil defines an axial lumen and has first and second vaso-occlusive coil windings in a proximal end portion thereof. The first and second windings define a vaso-occlusive coil opening therebetween. A distal end portion of the tubular member wall extends into the axial lumen of the vaso-occlusive coil. The locking pin extends through the vaso-occlusive coil opening and through the distal end portion of the tubular member wall disposed in the axial lumen of the vaso-occlusive coil, thereby locking the tubular member to the vaso-occlusive coil.

In some embodiments, the vaso-occlusive device delivery assembly also includes a stretch-resisting member disposed in the axial lumen of the vaso-occlusive coil, where a proximal end of the stretch-resisting member is coupled to the locking pin. The proximal end of the stretch-resisting member may also form a loop around the locking pin. In the some embodiments, the vaso-occlusive device delivery assembly also includes an adhesive securing the tubular member to the vaso-occlusive coil. The adhesive may be disposed within the axial lumen of the vaso-occlusive coil or within the vaso-occlusive coil opening between the first and second vaso-occlusive coil windings.

In some embodiments, the tubular member defines an axial lumen. A support coil may be disposed in the axial lumen of the tubular member. The support coil may have first and second support coil windings defining a support coil opening therebetween, where the locking pin further extends through the support coil opening. The support coil may be secured to the tubular member. In some embodiments, the locking pin has an external portion that extends laterally outward of the vaso-occlusive coil opening, and is sized and shaped to prevent passage thereof through the vaso-occlusive coil opening. The vaso-occlusive device delivery assembly may also include an adhesive that secures the external portion of the locking pin to the vaso-occlusive coil.

In another embodiment of the disclosed inventions, a vaso-occlusive device delivery assembly includes a pusher assembly, an elongate tubular member, a vaso-occlusive coil, and first and second locking pins. The pusher assembly defines a longitudinal axis. The elongate tubular member is attached to, and extends distally from, a distal end of the pusher assembly. The tubular member is aligned with the longitudinal axis of the pusher assembly and has a tubular member wall. The vaso-occlusive coil defines an axial lumen, a first opening between a first pair of windings, and a second opening between a second pair of windings. A distal end portion of the tubular member wall extends into the axial lumen of the vaso-occlusive coil. First and second locking pins extend through the first and second openings, respectively, and further extend through the distal end portion of the tubular member wall disposed in the axial lumen of the vaso-occlusive coil, thereby locking the tubular member to the vaso-occlusive coil.

In some embodiments, the vaso-occlusive device delivery assembly also includes a locking pin connector disposed adjacent an exterior surface of the vaso-occlusive coil. Each of first and second locking pins may have an external portion that extends laterally outward of respective first and second openings. The locking pin connector may be attached to the respective external portions of the first and second locking pins. The vaso-occlusive device delivery assembly may also include an adhesive that secures the first and second locking pins, and the locking pin connector, to the vaso-occlusive coil. In some embodiments, the first locking pin has an external portion comprising a hook that extends laterally outward of the opening, where a distal end of the hook extends into the second opening.

In yet another embodiment of the disclosed inventions, a vaso-occlusive device delivery assembly includes a pusher assembly, first and second elongate tubular members, a vaso-occlusive coil, and a locking pin. The pusher assembly defines a longitudinal axis. The first elongate tubular member is attached to, and extends distally from, a distal end of the pusher assembly. The first tubular member is aligned with the longitudinal axis of the pusher assembly and has a first tubular member wall. The vaso-occlusive coil defines a longitudinal axis. The second elongate tubular member is attached to, and extends proximally from, a proximal end of the vaso-occlusive coil. The second tubular member is aligned with the longitudinal axis of the vaso-occlusive coil and has a second tubular member wall defining an axial lumen. A distal end portion of the first tubular member wall extends into the axial lumen of the second tubular member. The locking pin extends through the second tubular member wall and the distal portion of the first tubular member wall disposed in the axial lumen of the second tubular member, thereby locking the first tubular member to the vaso-occlusive coil.

In still another embodiment of the disclosed inventions, a vaso-occlusive device delivery assembly includes a pusher assembly, an elongate tubular member, a vaso-occlusive coil, a link, and a locking pin. The pusher assembly defines a longitudinal axis. The elongate tubular member is attached to, and extends distally from, a distal end of the pusher assembly. The tubular member is aligned with the longitudinal axis of the pusher assembly and has a tubular member wall defining an axial lumen. The link is attached to, and extends proximally from, a proximal end of the vaso-occlusive coil. The link has a proximal end portion defining a link opening, and extending into the axial lumen of the tubular member wall. The locking pin extends through the link opening and through the distal end portion of the tubular member wall, thereby locking the tubular member to the respective link and vaso-occlusive coil.

In another embodiment of the disclosed inventions, a vaso-occlusive device delivery assembly includes a pusher assembly, an elongate tubular member, a vaso-occlusive coil, a stretch-resisting member, and a tubular marker. The pusher assembly defines a longitudinal axis. The elongate tubular member is attached to, and extends distally from, a distal end of the pusher assembly. The tubular member is aligned with the longitudinal axis of the pusher assembly and has a tubular member wall defining an axial tubular member lumen. The vaso-occlusive coil defines an axial vaso-occlusive coil lumen. A proximal end portion of the stretch-resisting member extends into the tubular member lumen at a distal end portion of the tubular member wall. The distal end portion of the tubular member wall extends into the vaso-occlusive coil lumen at a proximal end portion of the vaso-occlusive coil. The tubular marker is crimped around the proximal end portion of the vaso-occlusive coil, the distal end portion of the tubular member, and the proximal end portion of the stretch-resisting member, thereby locking the stretch-resisting member, the tubular member, and the vaso-occlusive coil together. In some embodiments, the vaso-occlusive device delivery assembly also includes an adhesive securing the stretch-resisting member, the tubular member, and the vaso-occlusive coil together.

In another embodiment of the disclosed inventions, a vaso-occlusive device delivery assembly includes a pusher assembly defining a longitudinal axis, a detachable member attached to, and extending distally from, a distal end of the pusher assembly, the detachable member being aligned with the longitudinal axis of the pusher assembly, a vaso-occlusive device, and a locking pin extending through the vaso-occlusive device and through a distal end portion of the detachable member, thereby locking the detachable member to the vaso-occlusive device.

In still another embodiment of the disclosed inventions, a vaso-occlusive coil delivery system includes a vaso-occlusive coil, a delivery wire assembly, and a link. The vaso-occlusive coil defines a coil lumen and has first and second coil windings in a proximal end portion thereof. The first and second coil windings define a coil opening therebetween. The delivery wire assembly defines a delivery wire lumen, and includes a delivery wire conduit and a delivery wire. The delivery wire is attached to the delivery wire conduit and extends through the delivery wire lumen distal of the delivery wire conduit. The delivery wire includes an electrolytic detachment zone. The link defines a link lumen and has link body including proximal and distal ends. The proximal end of the link body defines a link opening in communication with the link lumen. The distal end of the link body includes a link detent extending radially from the link body. A distal end portion of the delivery wire extends through the link opening and into the link lumen, such that the electrolytic detachment zone is located outside of the link lumen. A distal end portion of the link extends into the coil lumen. The link detent extends through the coil opening, thereby securing the link body and the delivery wire assembly to the vaso-occlusive coil.

In some embodiments, the link also includes a cap formed at the proximal end of the link body. The cap has a cross-sectional dimension larger than a cross-sectional dimension of the link body, such that, when the link body extends into the coil lumen, the cross-sectional dimension of the cap prevents the cap from extending into the coil lumen. The link opening may be in the cap. The link body may also define a radially directed link port in communication with the link lumen. The vaso-occlusive coil delivery system may also include an adhesive disposed in the link port and the link lumen, where the adhesive secures the distal end portion of the delivery wire to the link body.

Alternatively, or additionally, the link may also define a loop at the distal end of the link body, and the vaso-occlusive coil may also include a stretch-resisting member attached to a distal end of the vaso-occlusive coil, where a proximal end of the stretch-resisting member passes through the loop to thereby attach the distal end of the vaso-occlusive coil to the link. The link may have a cylindrical shape. An outer diameter of the link body may be about the same as a diameter of the coil lumen.

In some embodiments, the coil opening defined by the first and second coil windings is a first coil opening, and the link detent is a first link detent. The vaso-occlusive coil may have third and fourth coil windings in the proximal end portion thereof. The third and fourth coil windings may define a second coil opening therebetween. The distal end of the link body may include a second link detent extending radially from the link body. The second link detent may extend through the second coil opening, thereby also securing the link body and the delivery wire assembly to the vaso-occlusive coil.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

Figure 1:
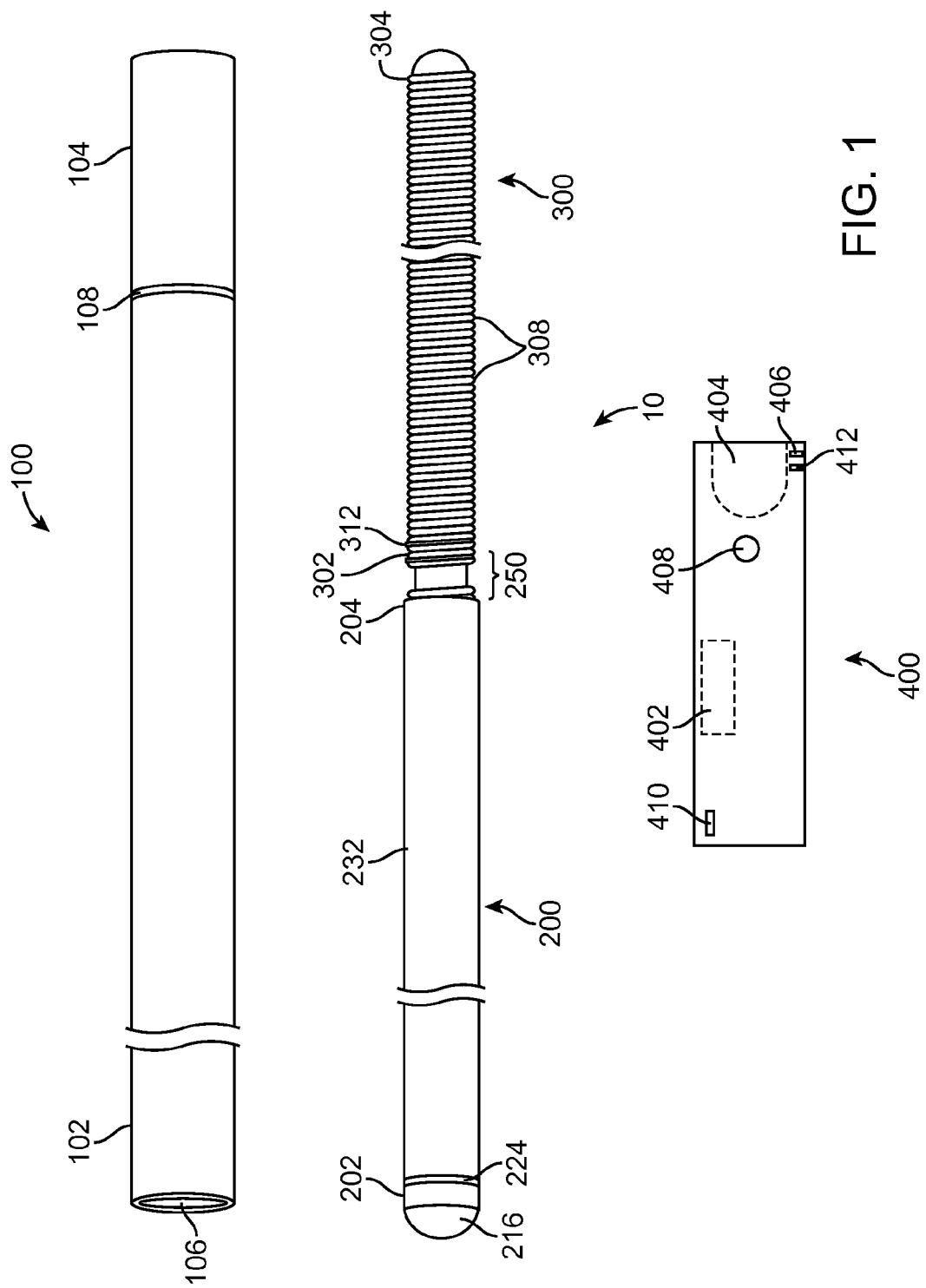
FIG. 1 is a schematic view of a vaso-occlusive device delivery system, according to one embodiment of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIG. 1 illustrates a vaso-occlusive device delivery system 10 according to an embodiment of the disclosed inventions. In the system 10 illustrated in FIG. 1, the vaso-occlusive device is a vaso-occlusive coil 300. The system 10 includes a number of subcomponents or sub-systems. These include a delivery catheter 100, a pusher assembly 200, a vaso-occlusive coil 300, and a power supply 400. The delivery catheter 100 includes a proximal end 102, a distal end 104, and a lumen 106 extending between the proximal and distal ends 102, 104. The lumen 106 of the delivery catheter 100 is sized to accommodate axial movement of the pusher assembly 200 and the vaso-occlusive coil 300. Further, the lumen 106 is sized for the passage of a guidewire (not shown) which may optionally be used to properly guide the delivery catheter 100 to the appropriate delivery site.

The delivery catheter 100 may include a braided-shaft construction of stainless steel flat wire that is encapsulated or surrounded by a polymer coating. By way of non-limiting example, HYDROLENE® is a polymer coating that may be used to cover the exterior portion of the delivery catheter 100. Of course, the system 10 is not limited to a particular construction or type of delivery catheter 100 and other constructions known to those skilled in the art may be used for the delivery catheter 100. The inner lumen 106 may be advantageously coated with a lubricious coating such as PTFE to reduce frictional forces between the delivery catheter 100 and the respective pusher assembly 200 and vaso-occlusive coil 300 being moved axially within the lumen 106. The delivery catheter 100 may include one or more optional tubular markers 108 formed from a radiopaque material that can be used to identify the location of the delivery catheter 100 within the patient's vasculature system using imaging technology (e.g., fluoroscope imaging). The length of the delivery catheter 100 may vary depending on the particular application, but generally is around 150 cm in length. Of course, other lengths of the delivery catheter 100 may be used with the system 10 described herein.

The delivery catheter 100 may include a distal end 104 that is straight as illustrated in FIG. 1. Alternatively, the distal end 104 may be pre-shaped into a specific geometry or orientation. For example, the distal end 104 may be shaped into a "C" shape, an "S" shape, a "J" shape, a 45° bend, a 90° bend. The size of the lumen 106 may vary depending on the size of the respective pusher assembly 200 and vaso-occlusive coil 300, but generally the OD of the lumen 106 of the delivery catheter 100 (I.D. of delivery catheter 100) is less than about 0.02 inches. The delivery catheter 100 is known to those skilled in the art as a microcatheter. While not illustrated in FIG. 1, the delivery catheter 100 may be utilized with a separate guide catheter (not shown) that aids in guiding the delivery catheter 100 to the appropriate location within the patient's vasculature.

Figure 3:
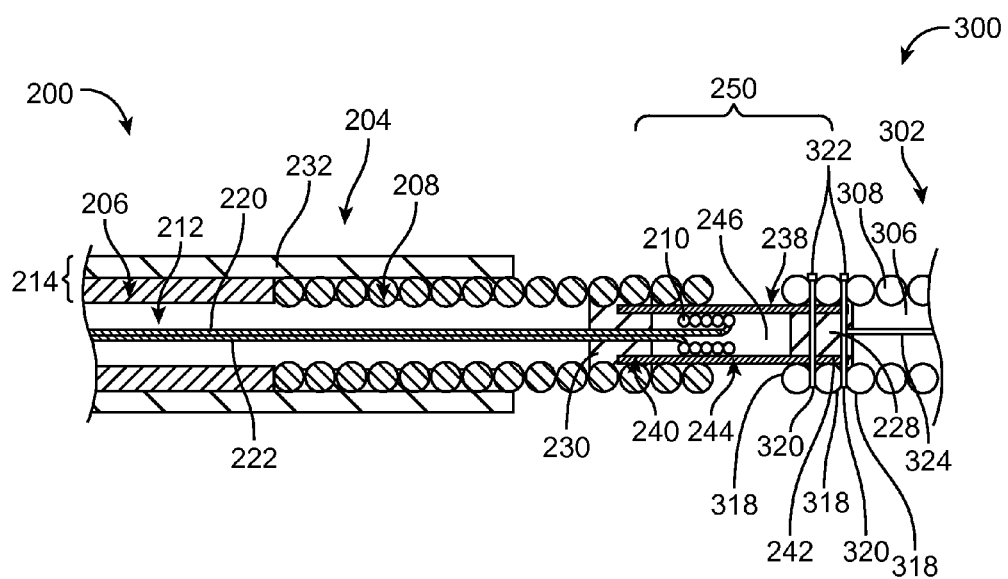
FIGS. 3-11 and 13-16 are detailed longitudinal cross-sectional views of vaso-occlusive device delivery systems according to various embodiments of the disclosed inventions, which depict the junction between the various pusher assemblies and vaso-occlusive coils.

As illustrated in FIGS. 1 and 3, the system 10 includes a pusher assembly 200 configured for axial movement within the lumen 106 of the delivery catheter 100. The pusher assembly 200 generally includes a proximal end 202 and a distal end 204. The pusher assembly 200 includes a pusher conduit 214, which has a proximal tubular portion 206 and a distal coil portion 208, and defines a pusher lumen 212 and a distal opening in communication with the pusher lumen 212.

FIG. 3 illustrates a detailed longitudinal cross-sectional view of the junction 250 between the pusher assembly 200 and the vaso-occlusive coil 300 according to one embodiment of the disclosed inventions. Similar elements of this embodiment are identified with the same reference numbers as discussed above with respect to FIG. 1. The pusher assembly 200 includes a proximal end 202 and a distal end 204 and measures between around 184 cm to around 186 cm in length. The proximal tubular portion 206 may be formed from, for example, a flexible stainless steel hypotube. The proximal tubular portion 206 may be formed from stainless steel hypotube having an OD of 0.01325 inches and inner diameter (ID) of 0.0075 inches. The length of the hypotube section may be between around 140 cm to around 150 cm, although other lengths may also be used.

A distal coil portion 208 is joined in end-to-end fashion to the distal face of the proximal tubular portion 206. The joining may be accomplished using a weld or other bond. The distal coil portion 208 may have a length of around 39 cm to around 41 cm in length. The distal coil portion 208 may comprise a coil of 0.0025 inches×0.006 inches. The first dimension generally refers to the OD of the coil wire that forms the coil. The latter dimension generally refers to the internal mandrel used to wind the coil wire around to form the plurality of coil winds and is the nominal ID of the coil. One or more windings of the distal coil portion 208 may be formed from a radiopaque material, forming marker coils. For example, the distal coil portion 208 may include a segment of stainless steel coil (e.g., 3 cm in length), followed by a segment of platinum coil (which is radiopaque and also 3 mm in length), followed by a segment of stainless steel coil (e.g., 37 cm in length), and so on and so forth.

An outer sleeve 232 or jacket surrounds a portion of the proximal tubular portion 206 and a portion of the distal coil portion 208 of the pusher conduit 214. Although the outer sleeve 232 depicted in FIG. 3 does not extend to the distal terminal end of the pusher assembly 200, in other embodiments the outer sleeve 232 can extend to the distal terminal end and distally beyond. The outer sleeve 232 covers the interface or joint formed between the proximal tubular portion 206 and the distal coil portion 208. The outer sleeve 232 may have a length of around 50 cm to around 54 cm. The outer sleeve 232 may be formed from a polyether block amide plastic material (e.g., PEBAX 7233 lamination). The outer sleeve 232 may include a lamination of PEBAX and HYDROLENE® that may be heat laminated to the pusher assembly 200. The OD of the outer sleeve 232 may be less than 0.02 inches and advantageously less than 0.015 inches. In embodiments where the pusher conduit 214 forms the negative conductor 222, the outer sleeve 232 is removed from the very distal end of the pusher conduit 214, during manufacturing, to form an exposed negative electrical contact 224.

As shown in FIG. 3, the system 10 also includes a tubular member 238 that detachably connects (i.e., releasably attaches) the vaso-occlusive coil 300 to the pusher assembly 200. The tubular member 238 has a proximal end 240 and a distal end 242, both of which are sealed, and a tube lumen 246 therebetween. The tubular member 238 may be made from biocompatible, heat degradable polymers with low melting points such as high-density polyethylene, low-density polyethylene, polypropylene, polyethylene terephthalate, and polycaprolactone.

The proximal end 240 of the tubular member 238 is disposed in the distal end of the pusher lumen 212. The open proximal end 240 of the tubular member 238 is attached to the pusher assembly 200 by a proximal seal 230, effectively closing the proximal end 240 of the tubular member 238. The proximal seal 230 is also attached to the interior surface of the pusher conduit 214 in the pusher lumen 212. The positive and negative conductors 220, 222 extend through the proximal seal 230 while the proximal seal 230 maintains a substantially fluid tight seal between regions proximal and distal of the proximal seal 230. The distal end 242 of the tubular member 238 is attached to the vaso-occlusive coil 300 in the proximal end of the vaso-occlusive coil lumen 306 by a distal seal 228. The proximal and distal seals 230, 228 may be formed from an adhesive.

The system 10 further includes a heat generating member 210 disposed in the tube lumen 246, between the proximal and distal seals 230, 228. The tubular member 238 insulates the environment external to the tubular member 238 from heat generated by the heat generating member 210. In the embodiment depicted in FIG. 3, the heat generating member 210 is a resistive heating coil 210 disposed in the distal end 204 of the pusher assembly 200. In other embodiments, the heat generating member 210 may include mechanical, inductive, magnetic, or optical mechanisms.

The resistive heating coil 210 is connected to positive and negative conductors 220, 222 disposed in the pusher lumen 212. The resistive heating coil 210 can be wound from platinum or Nichrome® (nickel chromium alloy) wire, such that when a current is delivered through the resistive heating coil 210 by the positive and negative conductors 220, 222 from the power supply 400, a resistance to the current flow generates heat in the resistive heating coil 210. The heating coil 210 can also be wound from carbon fibers. The resistive heating coil 210 may also have a variable pitch with a distal portion having a lesser pitch (more windings per unit length) than a proximal portion. A heating coil 210 with variable pitch would have non-uniform heat distribution with more heat at the distal and to accelerate melting or thermal degradation of the tubular member 238.

The positive and negative conductors 220, 222 may be formed from an electrically conductive material such as twisted copper wire coated with polyimide, with an OD of around 0.00175 inches. The proximal ends of the positive and negative conductors 220, 222 are electrically connected to positive and negative electrical contacts 216, 224, respectively. As shown in FIG. 1, positive and negative electrical contacts 216, 224 are located at the proximal end of the pusher assembly 200. The positive electrical contact 216 may be formed from a metallic solder (e.g., gold) that is configured to interface with a corresponding electrical contact (not shown) in the power supply 400 (described below). The negative electrical contact 224 may be an annular ring electrode disposed on top of an electrically insulative outer sleeve 232 at the proximal end of the pusher conduit 214 (described below). The positive and negative conductors 220, 222 may be coated with an insulative coating such as polyimide except where they connect to the positive and negative electrical contacts 216, 224, respectively.

Due to the proximity of the heating coil 210 to the tubular member 238 and the low melting point of the tubular member 238, when current is delivered through the heating coil 210 by the positive and negative conductors 220, 222, heat generated at the heating coil 210 melts or otherwise thermally degrades the tubular member 238, thereby detaching the vaso-occlusive coil 300 from the pusher assembly 200. This heat generated detachment is especially effective where, as in FIG. 3, the heating coil 210 is in contact with the tubular member 238.

Further, the tubular member 238 and the proximal and distal seals 230, 228 form a substantially fluid-tight chamber in the tube lumen 246. When the resistive heating coil 210 is activated as described above, wherein the fluid tight-chamber increases in temperature and pressure, facilitating bursting/severing the tubular member. This increase in pressure also pushes the detached vaso-occlusive coil 300 from the pusher assembly 200 with a positive thrust force. This pressure actuated detachment is described in the co-owned U.S. application Ser. No. 14/206,244, filed Mar. 12, 2014, the contents of which are fully incorporated herein by reference as though set forth in full.

Optionally, a detachment zone 244 between the proximal and distal ends 240, 242 of the tubular member 238 may be treated to facilitate severing of the tubular member 238. In some embodiments, the detachment zone 244 is under tension. In other embodiments, the detachment zone 244 may be either thermally or mechanically (e.g., perforated) treated to facilitate detachment.

The vaso-occlusive coil 300 includes a proximal end 302, a distal end 304, and a lumen 306 extending there between. The vaso-occlusive coil 300 is made from a biocompatible metal such as platinum or a platinum alloy (e.g., platinum-tungsten alloy). The vaso-occlusive coil 300 includes a plurality of coil windings 308. The coil windings 308 are generally helical about a central axis disposed along the lumen 306 of the vaso-occlusive coil 300.

The vaso-occlusive coils 300 depicted in FIGS. 1 and 3 have a substantially closed pitch configuration. However, the terminal proximal ends 302 of the vaso-occlusive coils 300 have open pitch windings 318 with spaces 320 therebetween. The open pitch windings 318 overlay the distal end 242 of the tubular member 238, which extends into the occlusive coil lumen 306. As shown in FIG. 3, locking pins 322 extend through the spaces 320 between open pitch windings 318 and pierce the distal end 242 of the tubular member 238. The locking pins 322 are held in position by an interference fit with the open pitch windings 318 and the distal end 242 of the tubular member 238. In the embodiment depicted in FIG. 3, the locking pins are also held in position by the adhesive forming the distal seal 228. Consequently, the locking pins 322 mechanically secure the distal end 242 of the tubular member 238 and the distal end 204 of the pusher assembly 200 to the vaso-occlusive coil 300. A stretch-resisting member 324, such as a suture, may be secured to the distal end 304 of the vaso-occlusive coil 300 and extend through the lumen 306 to the proximal end 302 where it is secured to a locking pin 322. In the embodiment depicted in FIG. 3, the stretch-resisting member 324 is looped around a locking pin 322.

Figure 2:
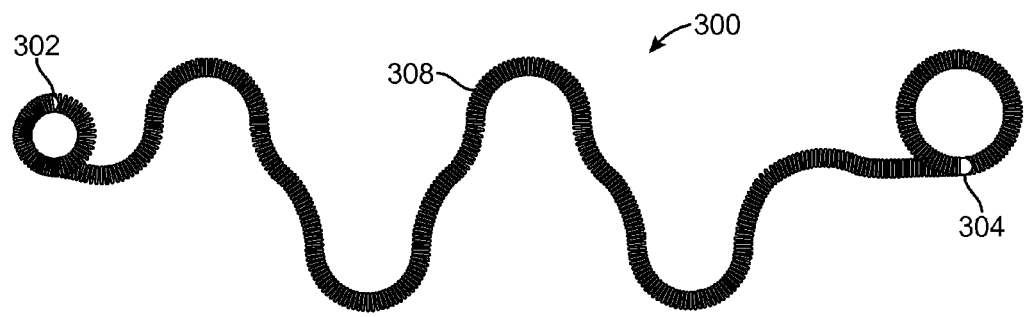
FIG. 2 is a side view of an occlusive coil in a natural state mode, illustrating one exemplary secondary configuration according to an embodiment of the disclosed inventions.

The vaso-occlusive coil 300 generally includes a straight configuration (as illustrated in FIG. 1) when the vaso-occlusive coil 300 is loaded within the delivery catheter 100. Upon release, the vaso-occlusive coil 300 generally takes a secondary shape which may include three-dimensional helical configurations. FIG. 2 illustrates one exemplary configuration of a vaso-occlusive coil 300 in a natural state. In the natural state, the vaso-occlusive coil 300 transforms from the straight configuration illustrated in, for instance, FIG. 1 into a secondary shape. The secondary shaped may include both two and three dimensional shapes of a wide variety. FIG. 2 is just one example of a secondary shape of a vaso-occlusive coil 300 and other shapes and configurations are contemplated to fall within the scope of the disclosed inventions. Also, the vaso-occlusive coil 300 may incorporate synthetic fibers (not shown) over all or a portion of the vaso-occlusive coil 300 as is known in the art. These fibers may be attached directly to coil windings 308 or the fibers may be integrated into the vaso-occlusive coil 300 using a weave or braided configuration. Of course, the system 10 described herein may be used with occlusive coils 300 or other occlusive structures having a variety of configurations, and is not limited to occlusive coils 300 having a certain size or configuration.

As shown in FIG. 1, the system 10 further includes a power supply 400 for supplying direct current to the positive and negative conductors 220, 222. Activation of the power supply 400 causes electrical current to flow in a circuit including the positive and negative conductors 220, 222 and the resistive heating coil 210. The power supply 400 preferably includes an onboard energy source, such as batteries (e.g., a pair of AAA batteries), along with drive circuitry 402. The drive circuitry 402 may include one or more microcontrollers or processors configured to output a driving current. The power supply 400 illustrated in FIG. 1 includes a receptacle 404 configured to receive and mate with the proximal end 202 of the delivery wire assembly 200. Upon insertion of the proximal end 202 into the receptacle 404, the positive, negative electrical contracts 216, 224 disposed on the delivery wire assembly 200 electrically couple with corresponding contacts (not shown) located in the power supply 400.

A visual indicator 406 (e.g., LED light) is used to indicate when the proximal end 202 of delivery wire assembly 200 has been properly inserted into the power supply 400. Another visual indicator 410 is activated if the onboard energy source needs to be recharged or replaced. The power supply 400 includes an activation trigger or button 408 that is depressed by the user to apply the electrical current to the resistive heating coil 210 via the positive and negative conductors 220, 222. Once the activation trigger 408 has been activated, the driver circuitry 402 automatically supplies current. The drive circuitry 402 typically operates by applying a substantially constant current, e.g., around 50-500 mA. A visual indicator 412 may indicate when the power supply 400 is supplying adequate current to the resistive heating coil 210.

In use, the vaso-occlusive coil 300 is attached to the pusher assembly 200 at junction 250. The attached vaso-occlusive coil 300 and pusher assembly 200 are threaded through the delivery catheter 100 to a target location (e.g., an aneurysm) in the patient's vasculature. Once the distal and 304 of the vaso-occlusive coil 300 reaches the target location, the vaso-occlusive coil 300 is pushed further distally until it's completely exits the distal and 104 of the delivery catheter 100.

In order to detach the vaso-occlusive coil 300 from the pusher assembly 200, the power supply 400 is activated by depressing the trigger 408. The drive circuitry 402 in the power supply 400 applies a current to the positive and negative conductors 220, 222 through the positive and negative electrical contacts 216, 224. As the applied current travels through the resistive heating coil 210, the resistive heating coil 210 generates heat. The generated heat raises the temperature of the tubular member 238 to its melting point, at which the tubular member 238 loses the structural integrity, becomes severed, and releases the vaso-occlusive coil 300 from the pusher assembly 200. After activation of the power supply 400, the vaso-occlusive coil 300 is typically detached in less than one second.

Further, the heat generated by the heating coil 210 increases the temperature and pressure of air in the substantially fluid-tight chamber facilitating severance of the tubular member to create and release of the vaso-occlusive coil 300 from the pusher assembly 200. Moreover, the vaso-occlusive coil 300 is ejected from the pusher assembly 200 by the increased pressure. This positive thrust force separating the vaso-occlusive coil 300 from the pusher assembly 200 ensures separation and prevents "sticky coils."

Figure 4:
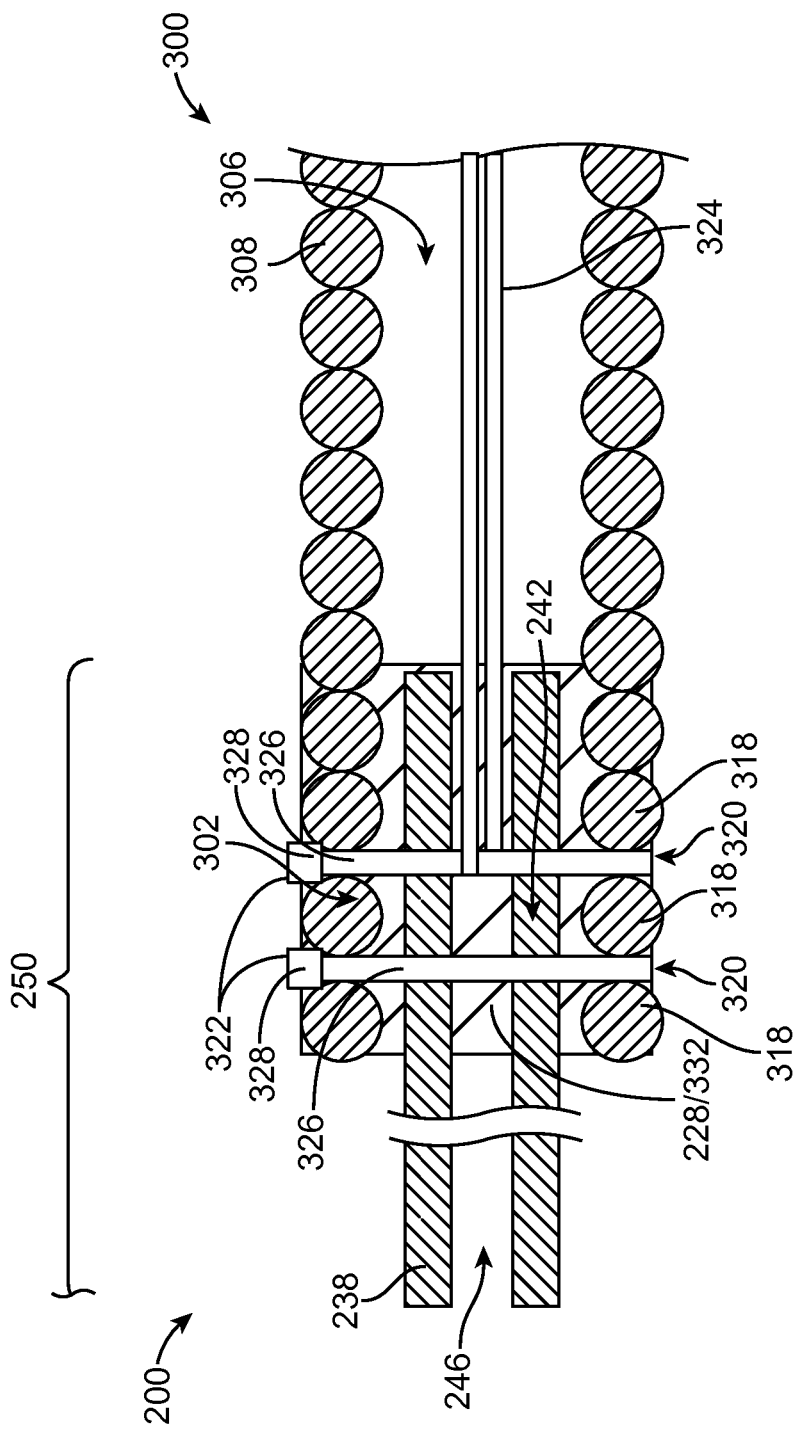

FIG. 4 is a detailed view of the junction 250 between the pusher assembly 200 and the vaso-occlusive coil 300 of the vaso-occlusive device delivery system 10 depicted in FIG. 3. Each of the pair of locking pins 322 depicted in FIG. 4 has an elongate portion 326 and an enlarged end portion 328. When the locking pins 322 are inserted into the spaces 320 between the open windings 318 and through the distal end 242 of the tubular member 238, the enlarged end portions 328 prevent the locking pins 322 from completely passing through the vaso-occlusive coil 300. Further, the proximal end of the stretch-resisting member 324 is looped around the elongate portion 326 of the distal most locking pin 322. As can be seen in FIG. 4, the locking pin 322 mechanically secures the tubular member 238 to the vaso-occlusive coil 300 and the stretch-resisting member 324 to the vaso-occlusive coil 300 and the tubular member 238.

This design particularly increases the tensile strength of the junction 250 between the pusher assembly 200 and the vaso-occlusive coil 300. In some embodiments, the tensile strength is around 0.3 lbs. The design also facilitates manufacturing of vaso-occlusive device delivery systems 10.

The vaso-occlusive device delivery systems 10 depicted in FIGS. 5 to 11 are similar to the system 10 depicted in FIGS. 3 and 4. Similar elements of this embodiment are identified with the same reference numbers as discussed above with respect to FIGS. 3 and 4.

Figure 5:
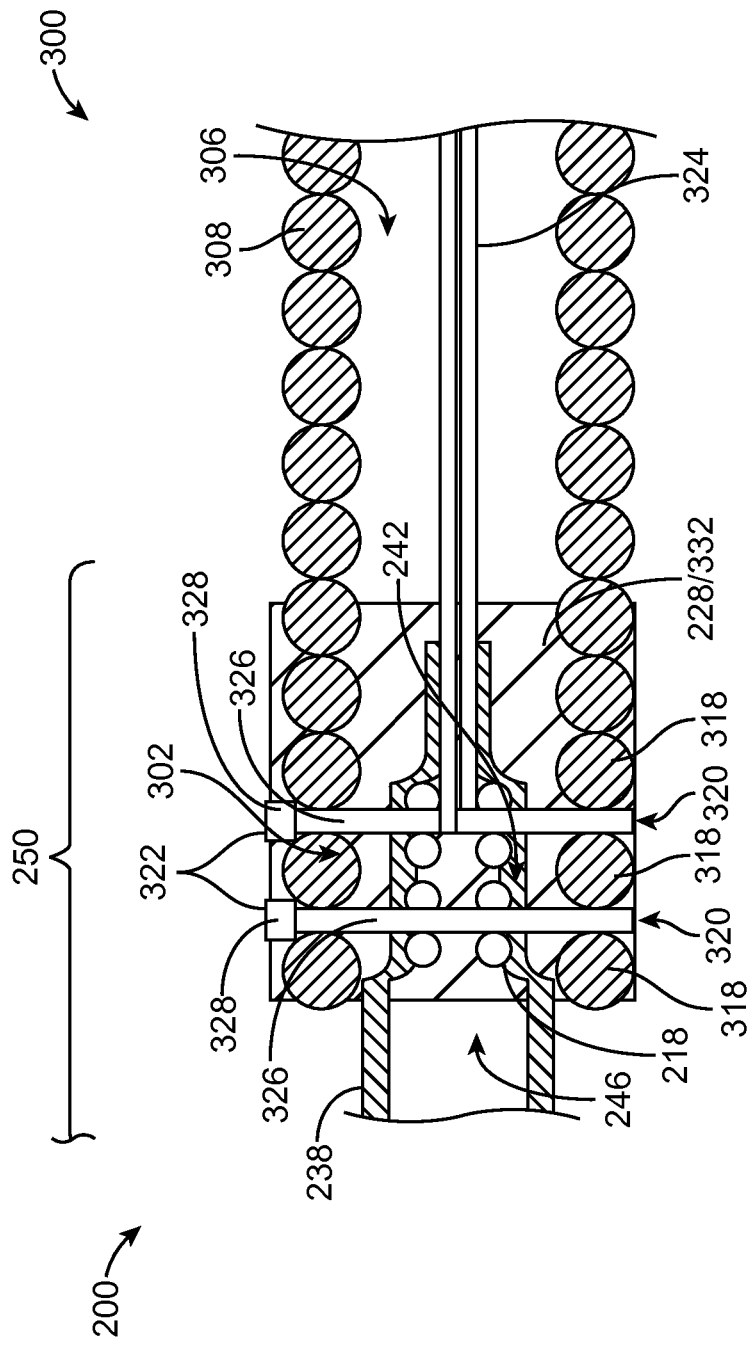

FIG. 5 depicts a junction 250 between the pusher assembly 200 and the vaso-occlusive coil 300 that is similar to the junction 250 depicted in FIG. 4. Like the junction 250 depicted in FIG. 4, a pair of locking pins 322 pass through the spaces 320 between the open windings 318 and the distal end 242 of the tubular member 238, thereby mechanically securing the tubular member 238 and the pusher assembly 200 to the vaso-occlusive coil 300. However, the vaso-occlusive device delivery systems 10 depicted in FIG. 5 includes a support coil 218 positioned in the lumen 246 of the tubular member 238. The support coil 218 has open windings sized to allow a locking pin 322 to be inserted therethrough. The tubular member 238 is shrunken (e.g., by heat) around the support coil 218, thereby mechanically securing the support coil 218 in the tubular member 238. When the locking pins 322 are inserted through the tubular member 238, they are also inserted through the open windings of the support coil 218 disposed in the distal end 242 of the tubular member 238. In this manner, the support coil 218 further strengthens the junction 250 between the pusher assembly 200 and the vaso-occlusive coil 300. Moreover, the terminal distal end of the tubular member 238 is shrunken (e.g., by heat) around the proximal end of the stretch-resisting member 324, thereby securing the stretch-resisting member 324 to the tubular member 238.

Figure 6:
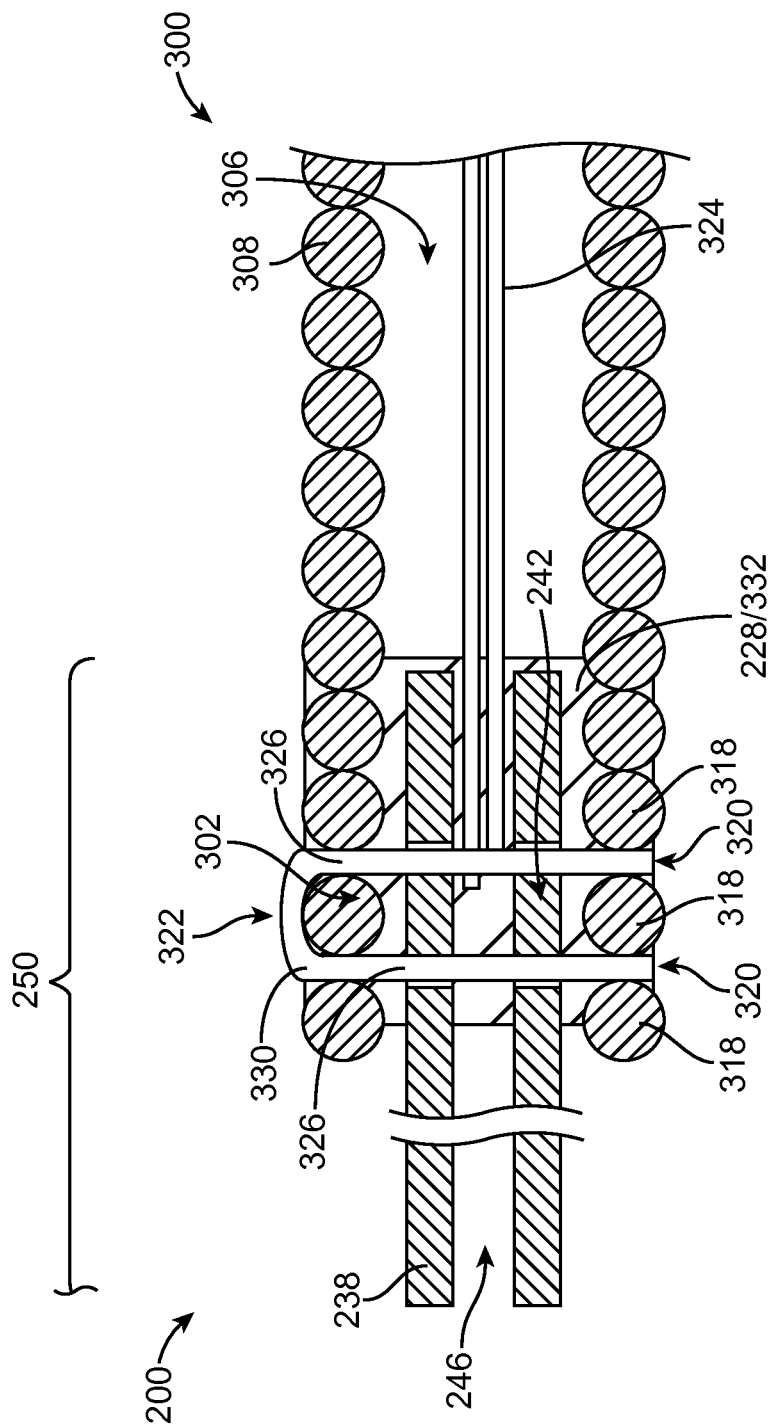

FIG. 6 depicts another junction 250 between the pusher assembly 200 and the vaso-occlusive coil 300 that is similar to the junction 250 depicted in FIG. 4. Instead of a pair of locking pins 322 each with an enlarged end portion 328, the vaso-occlusive device delivery systems 10 depicted in FIG. 6 includes a "U" shaped locking pin 322 with two elongate portions 326 connected by a connecting portion 330. The connecting portion 330 remains outside of the vaso-occlusive coil 300 and performs the same function as the enlarged end portion 328 depicted in FIG. 4, i.e., preventing the locking pin 322 from completely passing through the vaso-occlusive coil 300. The physical structure of the "U" shaped locking pin 322 eliminates the possibility that a locking pin 322 will completely slip through the vaso-occlusive coil 300.

Figure 7:
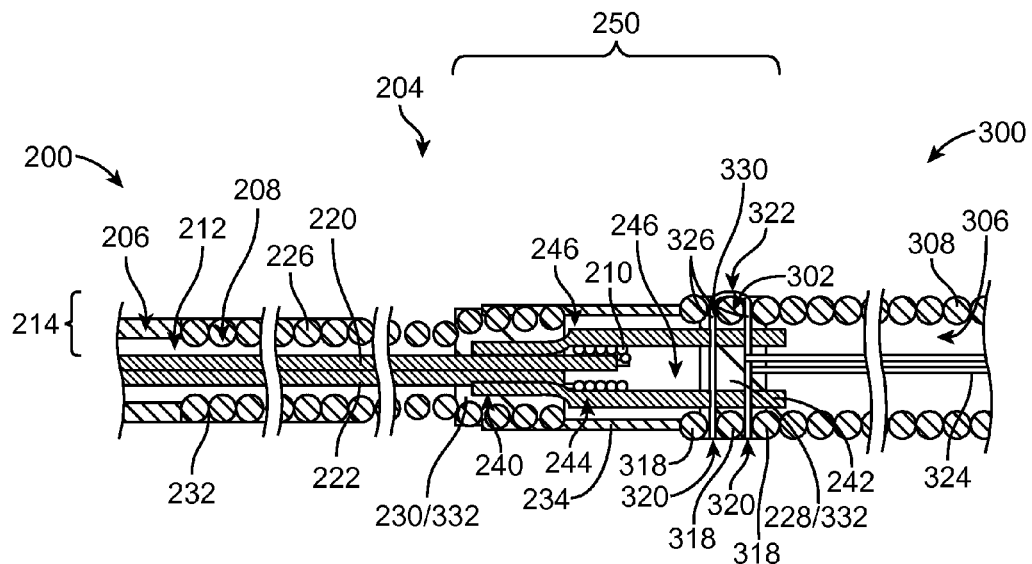

FIG. 7 depicts a vaso-occlusive device delivery system 10, similar to the one depicted in FIG. 3, except that the pair of locking pins 322 depicted in FIG. 3 has been replaced with a "U" shaped locking pin 322, as shown in FIG. 6 and described above. Further, the distal coil portion 208 of the pusher assembly 200 includes a set of marker coils 226 for fluoroscopic visualization. In addition, the distal end of the distal coil portion 208 is tapered outward and has open pitch windings to allow adhesive 332 to enter to form the proximal seal 230. Moreover, the junction 250 includes a PTFE sleeve 234 disposed around the detachment zone 244.

Figure 8:
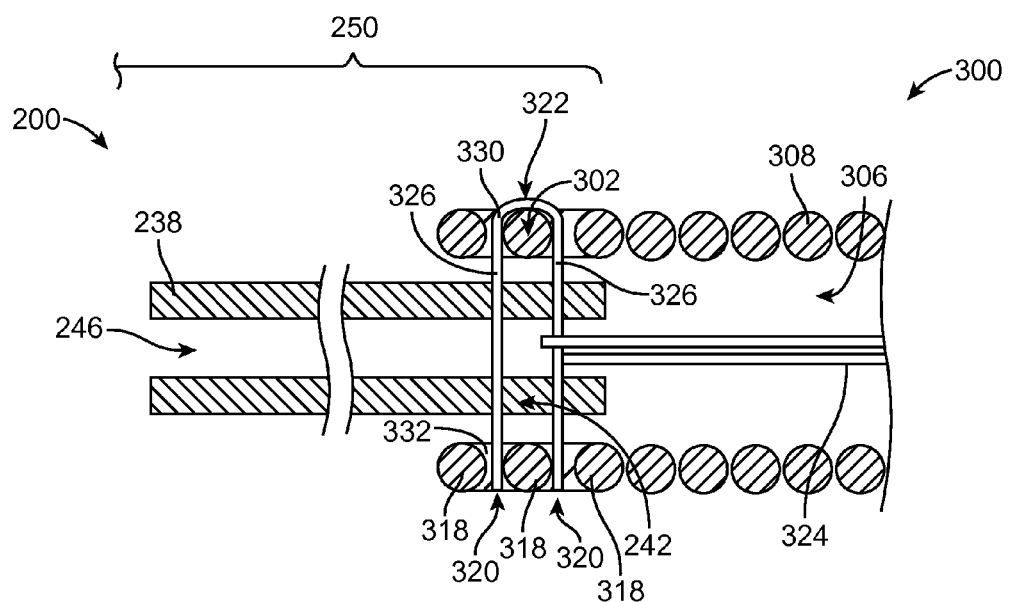

FIG. 8 depicts a junction 250 between the pusher assembly 200 and the vaso-occlusive coil 300 that is almost identical to the junction 250 depicted in FIGS. 6 and 7. Like the junction 250 depicted in FIGS. 6 and 7, the junction 250 depicted in FIG. 8 has a "U" shaped locking pin 322. The difference is that the junction 250 depicted in FIG. 8 includes a tubular member 238 with an open distal end 242. The junction 250 does not include a distal seal 228, however a small amount of adhesive 332 is disposed in the spaces 320 between the open windings 318 of the vaso-occlusive coil 300 to secure the "U" shaped locking pin 322 to the vaso-occlusive coil 300. The design depicted in FIG. 8 has enhanced flexibility compared to the design depicted in FIGS. 6 and 7 because of the removal of the distal seal 228 and the reduced amount of adhesive 332.

Figure 9:
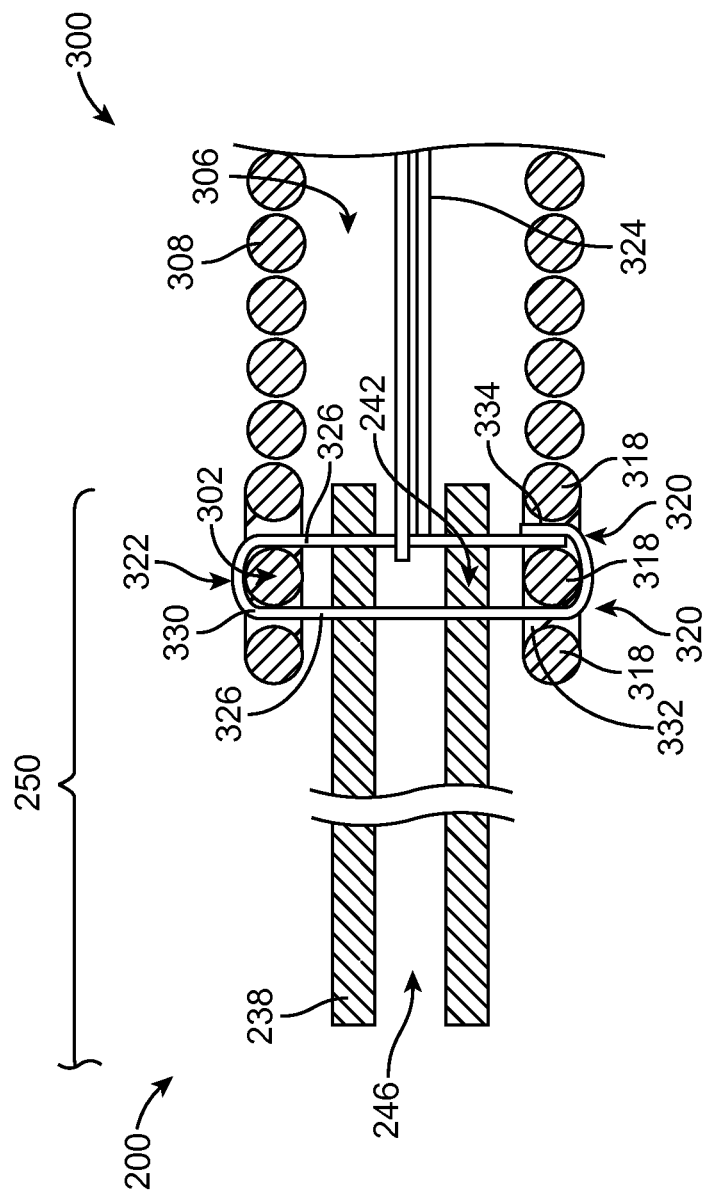

FIG. 9 depicts a junction 250 between the pusher assembly 200 and the vaso-occlusive coil 300 that is similar to the junction 250 depicted in FIG. 8. Like the junction 250 depicted in FIG. 8, the junction 250 depicted in FIG. 9 has a tubular member 238 with an open distal end 242. The difference is that the locking pin 322 depicted in FIG. 9 is shaped like a paper clip with a connection portion 330 and a hook portion 334 connected by one of two elongate portions 326. That elongate portion 326 extends through the vaso-occlusive coil 300 such that the connection portion 330 and the hook portion 334 are on opposite sides of the vaso-occlusive coil 300. The hook portion 334 exits from the vaso-occlusive coil 300 through one space 320 and reenters the vaso-occlusive coil 300 through another space 320, thereby further securing the locking pin 322 to the vaso-occlusive coil 300.

Figure 10:
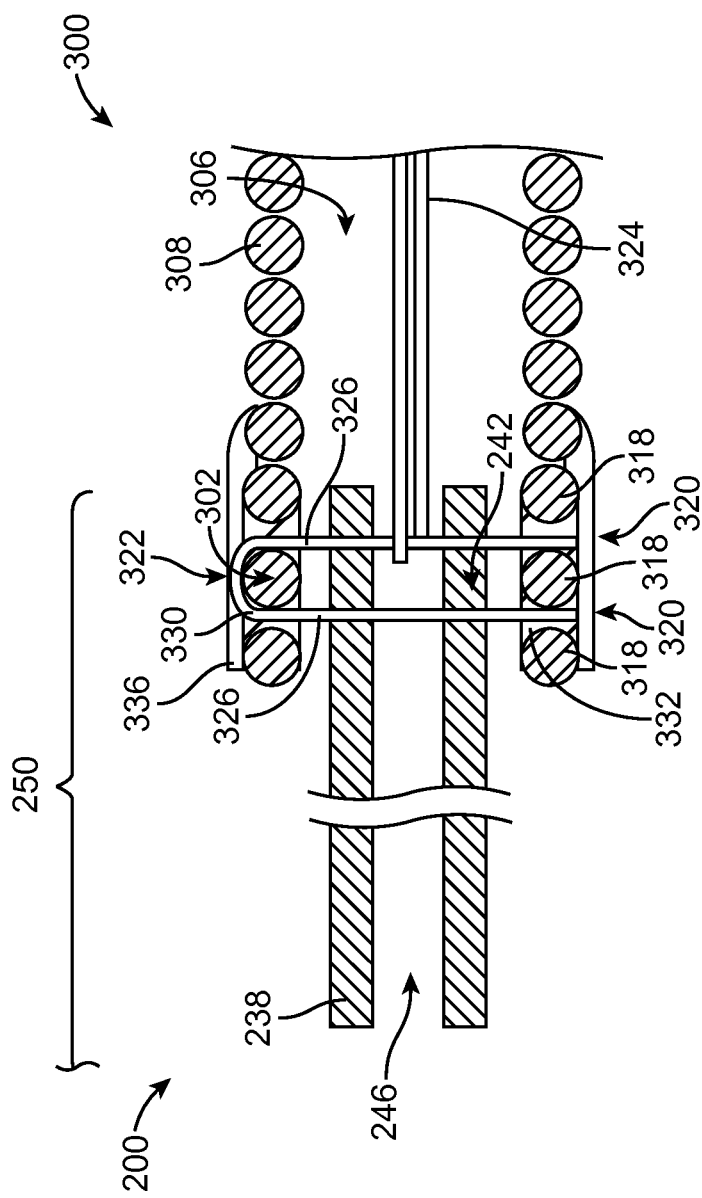

FIG. 10 depicts another junction 250 between the pusher assembly 200 and the vaso-occlusive coil 300 that is similar to the junction 250 depicted in FIG. 8. Like the junction 250 depicted in FIG. 8, the junction 250 depicted in FIG. 10 has a "U" shaped locking pin 322 and a small amount of adhesive 332 disposed in the spaces 320 between the open windings 318 of the vaso-occlusive coil 300. The difference is that a polymer layer 336 (e.g., polyethylene terephthalate) is deposited onto the exterior surface of the vaso-occlusive coil 300, covering locking pin 322. The polymer layer 336 may form a tubular body. The polymer layer 336 prevents radial movement of the locking pin 322, thereby further securing the locking pin 322 to the vaso-occlusive coil 300.

Figure 11:
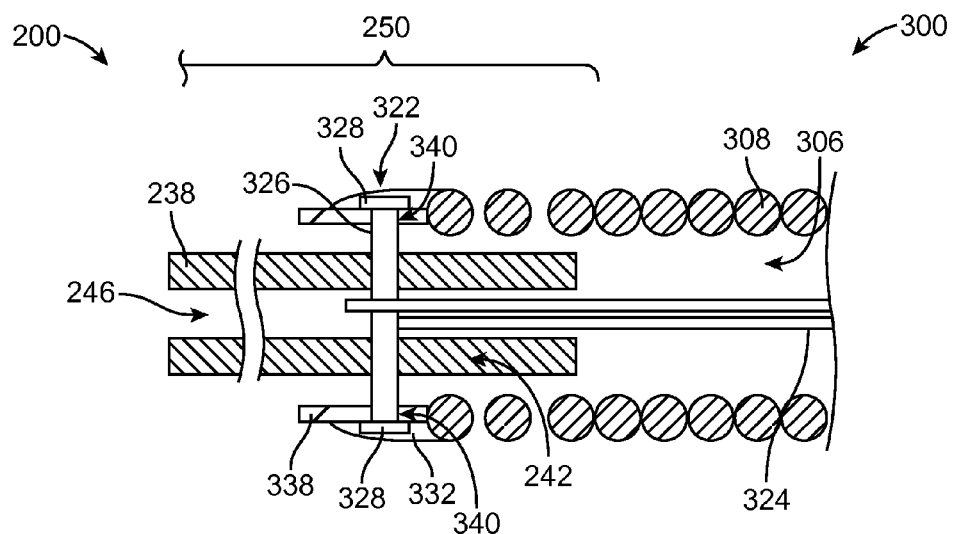

FIG. 11 depicts a junction 250 between the pusher assembly 200 and the vaso-occlusive coil 300 that is similar to the junction 250 depicted in FIG. 8. Like the junction 250 depicted in FIG. 8, the junction 250 depicted in FIG. 11 has a tubular member 238 with an open distal end 242. However, the junction 250 depicted in FIG. 11 has only a single locking pin 322. The locking pin 322 has an elongate portion capped on both ends by respective enlarged end portions 328. These enlarged end portions 328 may be formed by a mechanical process, such as applying pressure to the two ends of the locking pin 322. Another difference is that a metal tube 338 is added to the proximal end of the vaso-occlusive coil 300 (e.g., by welding). The metal tube 338 includes a pair of opposing openings 340 through which the locking pin passes 322, thereby anchoring the locking pin 322 and the tubular member 238 to the metal tube 338 and the vaso-occlusive coil 300.

Figure 12:
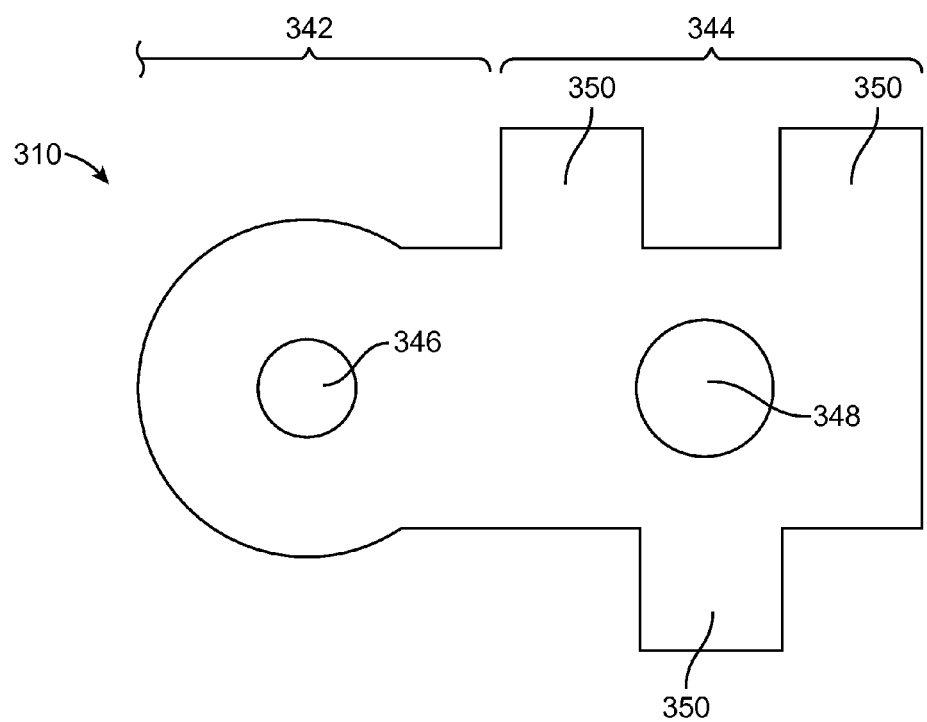
FIG. 12 is a side view of a link for connecting a pusher assembly to a vaso-occlusive coil according to an embodiment of the disclosed inventions.
Figure 13:
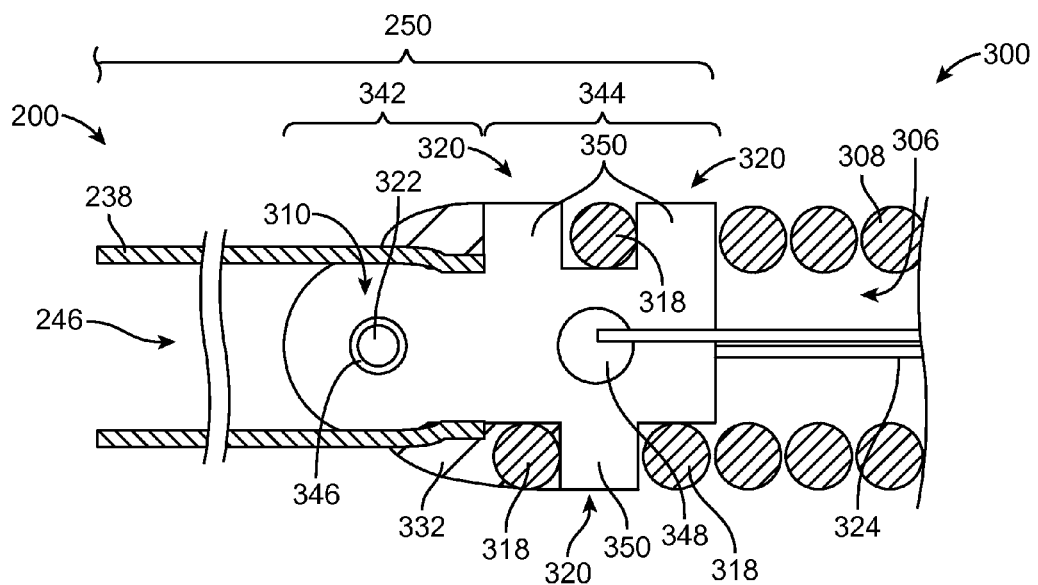
Figure 14:
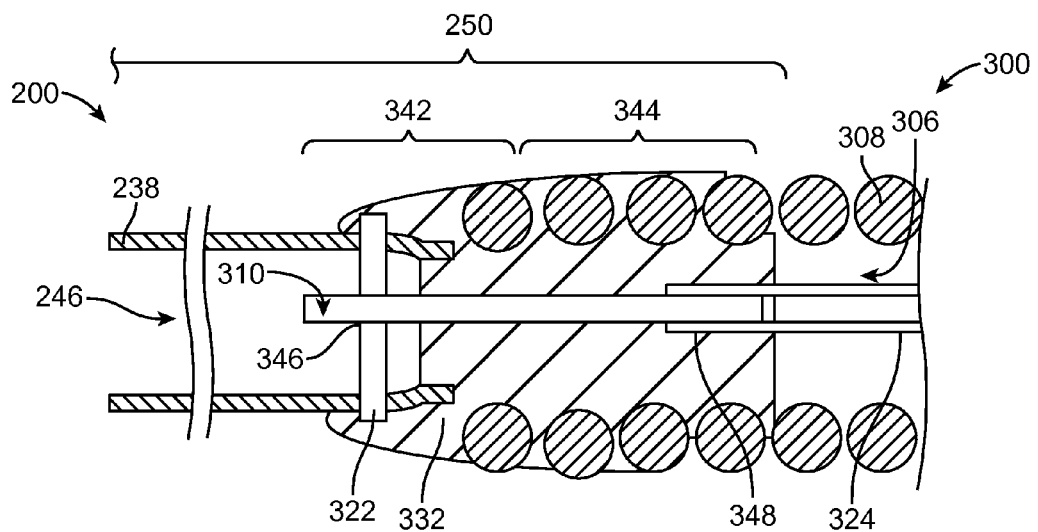

FIGS. 12-14 depict a link 310 and a junction 250 between the pusher assembly 200 and the vaso-occlusive coil 300 including a link 310. The link 310 (shown in isolation in FIG. 12) is a flattened body having has proximal and distal portions 342, 344. The link 310 defines proximal and distal openings 346, 348 in its respective proximal and distal portions 342, 344, and a plurality of fingers 350 in its distal end 344. The link 310 may be formed from a non-conductive material.

The distal portion 344 of the link 310 is secured to the vaso-occlusive coil 300 at the proximal end 302 thereof. The proximal end 302 of the vaso-occlusive coil 300 includes open pitch windings 318 with spaces 320 therebetween. The fingers 350 at the distal end 344 of the link 310 are interlaced into the spaces 320 between the open pitch windings 318. Mechanical interference between the fingers 350 and the open pitch windings 318 secure the link 310 to the vaso-occlusive coil 300.

A stretch-resisting member 324, such as a suture, is secured to the distal end 304 of the vaso-occlusive coil 300 and extends through the lumen 306 to the proximal end 302 where it is secured to the link 310. The stretch-resisting member 324 is secured by looping through the distal opening 348 of the link 310.

The proximal portion 342 of the link 310 is secured to the tubular member 238 by a locking pin 322. As shown in FIGS. 13 and 14, the proximal portion 342 of the link 310 is inserted into the tube lumen 246 at the distal end 242 of the tubular member 238. A locking pin 322 is inserted through the tubular member and the proximal opening 346 in the link, thereby securing the link 310 to the tubular member 238. An adhesive 332 is disposed inside and outside of the junction 250, further securing the tubular member 238, locking pin 322, link 310, vaso-occlusive coil 300, and stretch-resisting member 324 together.

Figure 15:
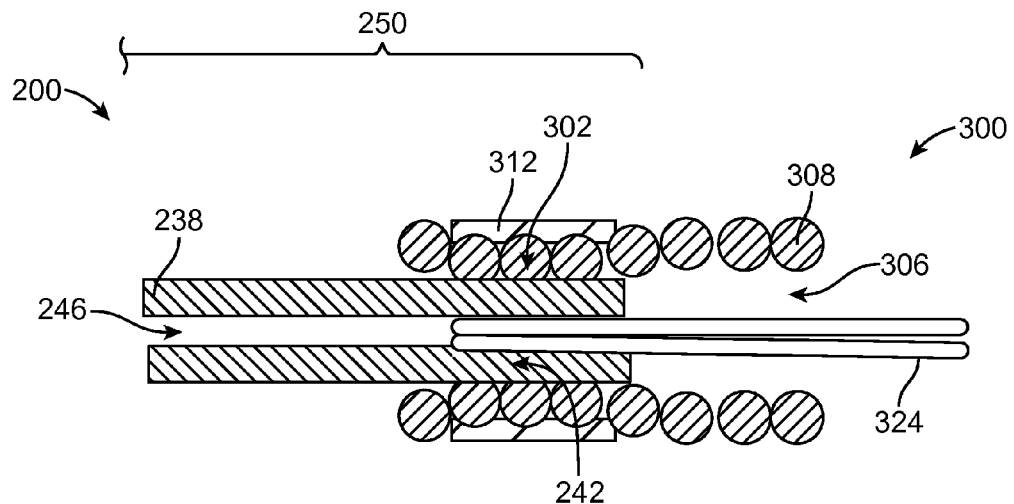
Figure 16:
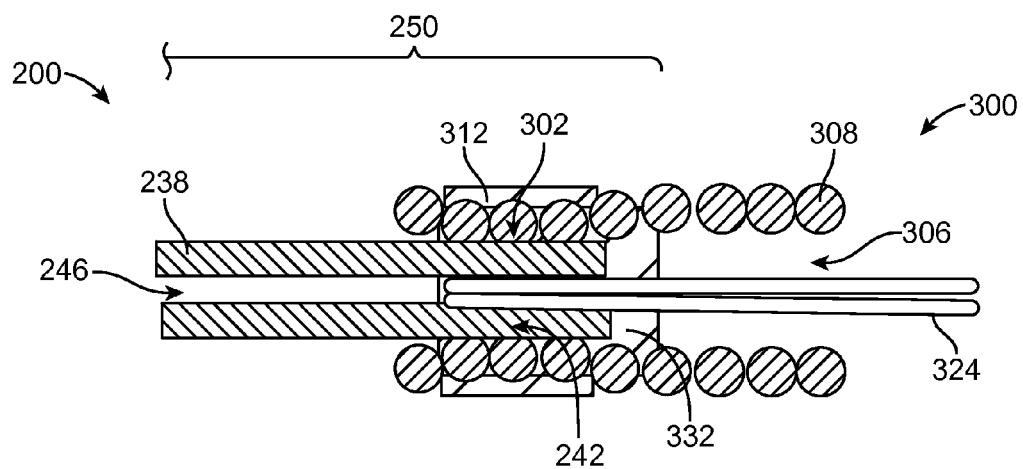

FIGS. 15 and 16 depict two junctions 250 between respective pusher assemblies 200 and vaso-occlusive coils 300, each junction 250 including a tubular marker 312. The proximal end of the stretch-resisting member 324 is disposed in the lumen 246 of the tubular member 238 at the distal end 242 thereof. The distal end 242 of the tubular member 238 is, in turn, disposed in the lumen 306 of the vaso-occlusive coil 300 at the proximal end 302 thereof. A tubular marker 312 is crimped around the proximal end 302 of the vaso-occlusive coil 300, the distal end 242 of the tubular member 238, and the proximal end of the stretch-resisting member 324 to mechanically secure the vaso-occlusive coil 300, the tubular member 238, and the stretch-resisting member 324 to each other. The tubular marker 312 may be made of a radiopaque material, such as platinum or iridium. In the junction depicted in FIG. 16, an adhesive 332 is disposed in the vaso-occlusive lumen 306 to further secure the vaso-occlusive coil 300, the tubular member 238, and the stretch-resisting member 324 together.

Figure 17:
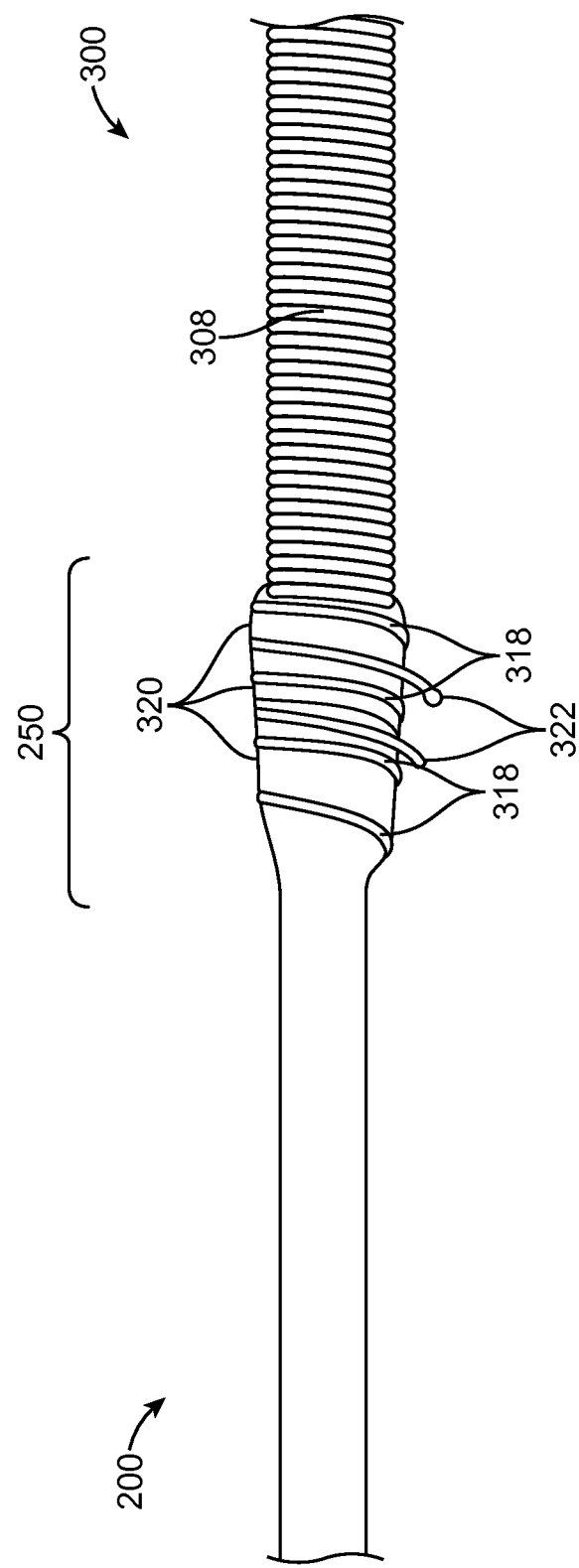
FIG. 17 is a side view photograph of a junction between the pusher assembly and the vaso-occlusive coil according to another embodiment of the disclosed inventions.

FIG. 17 is a side view photograph of a junction 250 between the pusher assembly 200 and the vaso-occlusive coil 300 according to another embodiment of the disclosed inventions. The junction 250 includes opening windings 318 defining spaces 320 therebetween. The junction also includes locking pins 322 disposed in the spaces 320.

Figure 18:
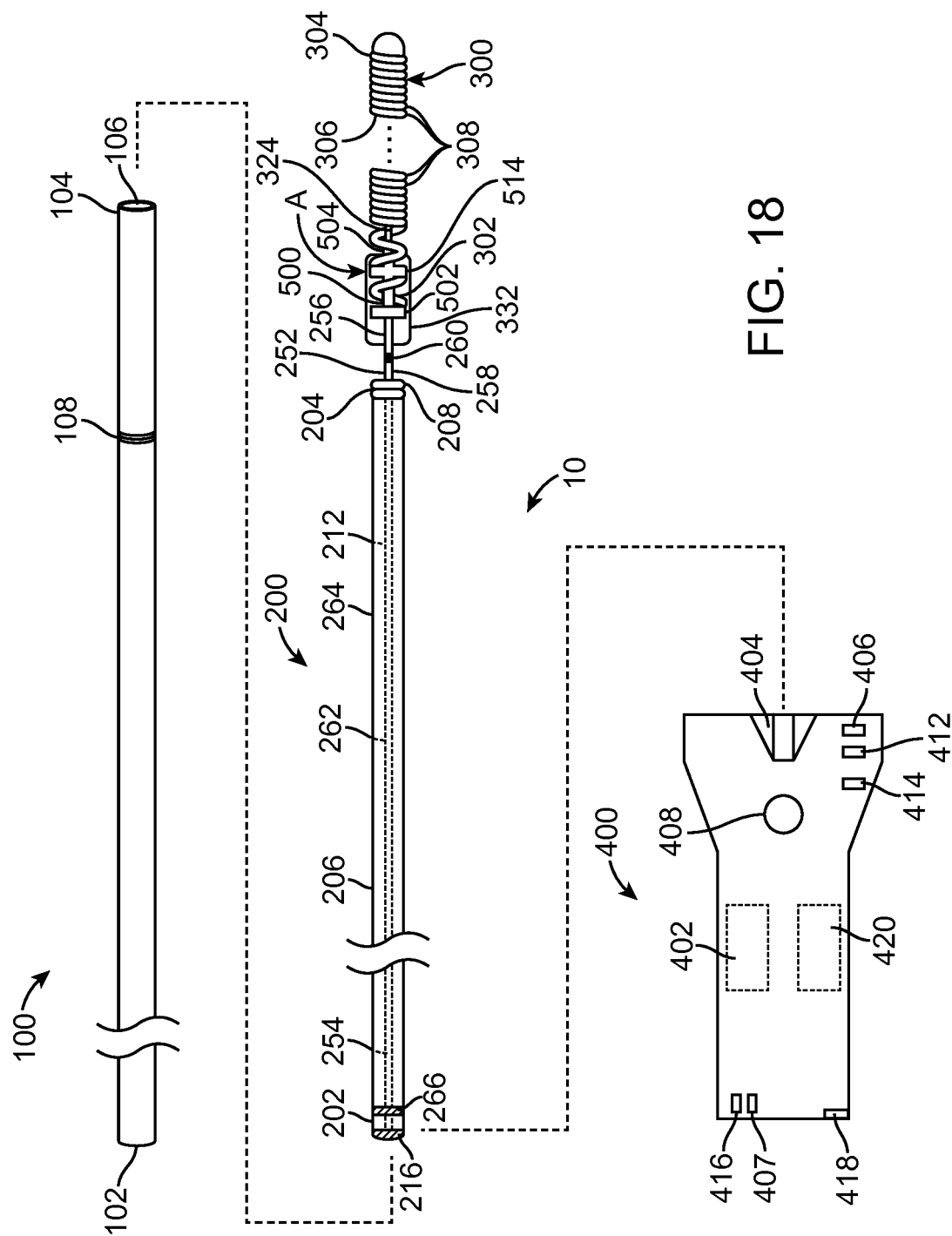
FIG. 18 is a schematic view of a vaso-occlusive device delivery system, according to another embodiment of the disclosed inventions.

FIG. 18 depicts a vaso-occlusive coil delivery system 10 according to another embodiment of the disclosed inventions. The vaso-occlusive coil delivery system 10 depicted in FIG. 18 is similar in some aspects to the one depicted in FIG. 1. One major difference is that the system 10 depicted in FIG. 18 includes an electrolytic detachment system, whereas the one depicted in FIG. 1 includes a thermal detachment system. To that end, the system 10 in FIG. 18 includes a pusher assembly 200 having a core wire 252, having proximal and distal ends 254, 256. The core wire 252 that extends from the proximal end 202 of the delivery wire assembly 200 to a location that is distal with respect to the distal end 204 of the delivery wire assembly 200. The core wire 252 is disposed within a lumen 212 that extends within an interior portion of the delivery wire assembly 200.

The core wire 252 is formed from an electrically conductive material such as stainless steel wire. The proximal end 214 of the core wire 252 (shown in phantom) is electrically coupled to an electrical contact 216 located at the proximal end 202 of the delivery wire assembly 200. The electrical contact 216 may be formed from a metallic solder (e.g., gold) that is configured to interface with a corresponding electrical contact (not shown) in the power supply 400. A portion of the core wire 252 is advantageously coated with an insulative coating 258. The insulative coating 258 may include polyimide. In one embodiment, the entire length of the core wire 252 is coated with an insulative coating 258 except for a small region 260 located in portion of the core wire 252 that extends distally with respect to the distal end 204 of the of the delivery wire assembly 200. This "bare" portion of the core wire 252 forms the electrolytic detachment zone 260 which dissolves upon application of electrical current from the power supply 400.

Figure 19:
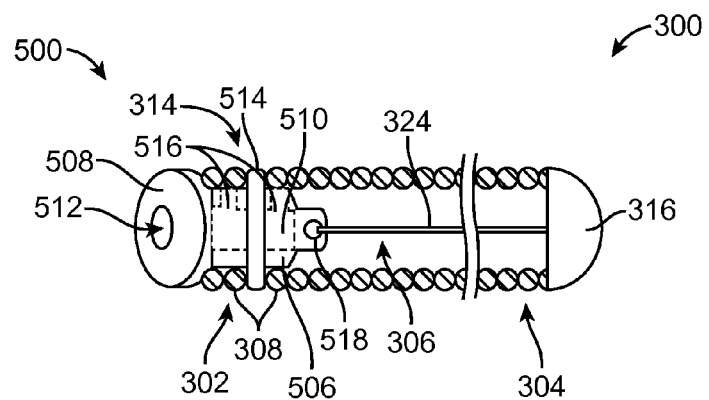
FIGS. 19 and 21 are detailed schematic views of vaso-occlusive coils with a link secured thereto, according to various embodiments of the disclosed inventions.
Figure 20:
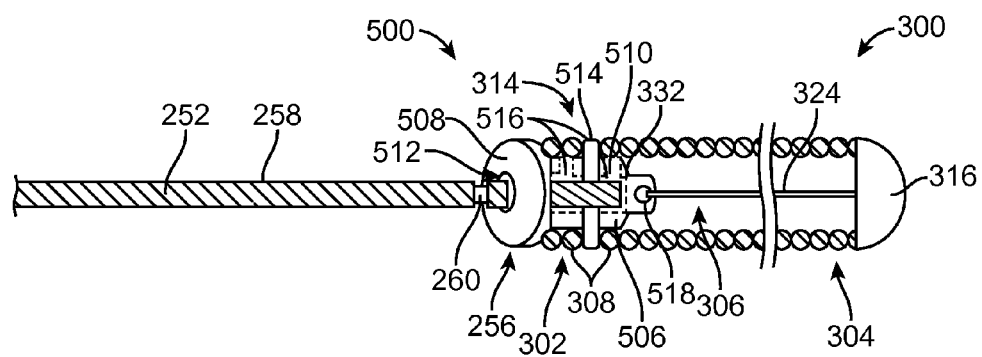
FIGS. 20 and 23 are detailed schematic views of vaso-occlusive device delivery systems according to various embodiments of the disclosed inventions, which depict the junction between the various pusher assemblies and vaso-occlusive coils, with the proximal tubular portion of the pusher assembly omitted for clarity.
Figure 21:
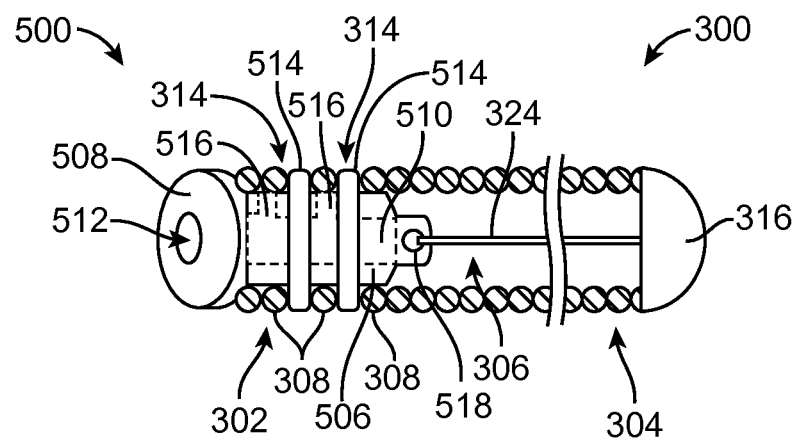

Another difference between the vaso-occlusive coil delivery system 10 depicted in FIG. 18 and the one depicted in FIG. 1 is that the system 10 depicted in FIG. 18 includes a link 500. An occlusive coil 300 is shown in FIG. 18 as being secured to the pusher assembly 200 via a delivery wire adapter 500. The link 500 has a proximal end 502 and a distal end 504, and includes a link body 506 and a cap 508 at the proximal end 502 thereof (best seen in FIGS. 19-23). The link 500 defines a radially centered link lumen 510 and a link opening 512 in communication with the link lumen 510 in the proximal end 502 of the link 500. As shown in FIGS. 19 and 21, the link opening 512 is in the cap and concentric therewith. The link 500 also defines a pair of link detents 514 extending radially from the link body 506. The detents 514 are configured to interface with the vaso-occlusive coil 300. The link 500 also forms an aperture 518 at its distal end 504.

The link 500 may be made from suitable materials such as polymers, stainless steel, iridium, platinum, gold, rhenium, tungsten, palladium, rhodium, and tantalum. The link 500 may be injection molded or cut (i.e., micro-machined) from blocks of suitable materials. Although any materials can be used to form the link 500, radiopaque materials are preferred due to their fluoroscopic visibility during use to allow the clinicians to precisely place and detach the embolic coil relatively to the treatment site (e.g., aneurysm/AVM).

Because the link 500 is compressible, it can be easily inserted or positioned into the proximal end of the coil lumen 306 and secured to the vaso-occlusive coil 300, while minimizing bending of and damage to the coil 300. Further, the outer diameter of the link body 506 is about the same as the diameter of the coil lumen 306, thereby centering the link 500 with respect to the vaso-occlusive coil 300.

FIG. 19 depicts a link 500 secured to a vaso-occlusive coil 300 according to one embodiment of the disclosed inventions. As described above, the occlusive coil 300 includes a plurality of coil windings 308. The coil windings 308 are generally helical about a central axis disposed along the lumen 306 of the occlusive coil 300. The proximal end 302 of the occlusive coil 300 has coil windings 308 with an open pitch configuration. For example, several of the proximal coil windings 308 may be spread open in the open pitch configuration (illustrated by arrow A in FIG. 18). The remaining distal portion of the occlusive coil 300 may have a closed pitch configuration as illustrated in FIGS. 18 and 19. Of course, the distal portion of the occlusive coil 300 may also include one or more open pitch segments or regions (or the entire occlusive coil 300 may be open pitched). The open pitch of the proximal coil windings 308 defines a coil opening 314 for the interface fit with the detents 514 of the link 500.

While the detents 514 of the link 500 do secure the link 500 to the vaso-occlusive coil 300, an adhesive 332 may also be applied to the interface between the link 500 and the proximal coil windings 308 of the occlusive coil 300. The adhesive 332 may include an epoxy material which is cured or hardened through the application of heat or UV radiation. For example, the adhesive 332 may include a thermally cured, two-part epoxy such as EPO-TEK® 353ND-4 available from Epoxy Technology, Inc., 14 Fortune Drive, Billerica, Mass. The adhesive 332 encapsulates and locates the link 500 substantially concentrically relative to the occlusive coil 300 and prevents tangential motion that may be induced by axially tensile loading of the occlusive coil 300.

As an alternative to the use of an adhesive 332, adjacent coil windings 308 on either side of the detents 514 may be joined by laser tack, spot, or continuous welding. Alternatively, laser melting of the detents 514 over the coil windings 308 may be used to mechanically join the link 500 to the occlusive coil 300.

Still referring to FIG. 19, the link body 506 also defines radially directed link ports 516 in communication with the link lumen 510. As shown in FIG. 20, when the distal end 256 of a core wire 252 is inserted into the link lumen 510 via the link opening 512, an adhesive 332 can be introduced into the link lumen 510 via the link ports 516. The adhesive 332 bonds the distal end 256 of a core wire 252 to the link 500. In this way, the distal end 256 of the core wire 252 can be secured to the link 500 without having to bend, and therefore weaken, the core wire 252.

FIGS. 19 and 20 also depict a stretch-resisting member 324 disposed in the vaso-occlusive coil lumen 306 and having proximal and distal ends. The proximal end of the stretch-resisting member 324 is secured the link 500 and the distal end of the stretch-resisting member 324 is attached to the distal end 304 of the vaso-occlusive coil 300. The stretch-resisting member 324 includes a distal cap 316. The stretch-resisting member 324 may take the form of a filament or the like. For example, the stretch-resisting member 324 may be formed from a polymeric material such as, for instance, suture filament material. During assembly of the occlusive coil 300, the stretch-resisting member 324 exists initially as only a single filament that extends from the distal cap 316. The free end of this filament is fed through the aperture 518 located at the distal end 504 of the link 500. The free end of the stretch-resisting member 324 is then pulled back toward the distal end 304 of the vaso-occlusive coil 300 where the same is bonded to the distal cap 316 to form the complete structure as illustrated in FIGS. 19 and 20. Heat bonding may be used to fuse or otherwise secure the free end of the stretch-resisting member 324 to the distal cap 316. Of course, other bonding techniques may also be used depending on the nature of the material used for the stretch-resisting member 324. These include, for instance, welding, adhesive bonding, and the like. The use of a stretch-resisting member 324 is entirely optional, however. Other embodiments may utilize an occlusive coil 300 that does not contain a stretch-resisting member 324.

Referring to FIG. 18, the proximal tubular portion 206 and a distal coil portion 208 form a return electrode for the delivery system 10. In this regard, the core wire 252 forms a first conductive path 262 between the electrical contact 216 and the electrolytic detachment zone 220. This first conductive path 262 may comprise the anode (+) of the electrolytic circuit when the delivery wire assembly 200 is operatively coupled to the power supply 400. A second conductive path 264 is formed by the proximal tubular portion 206 and a distal coil portion 208 of the delivery wire assembly 200. The second conductive path 264 is electrically isolated from the first conductive path 242. The second conductive path 244 may comprise the cathode (−) or ground electrode for the electrical circuit.

An electrical contact 266 for the second conductive path 264 may be disposed on a proximal end of the tubular portion 206. In one embodiment, the electrical contact 266 is simply an exposed portion of the tubular portion 206 since the tubular portion 206 is part of the second conductive path 264. For instance, a proximal portion of the tubular portion 206 that is adjacent to the electrical contact 216 may be covered with an insulative coating 258 such as polyimide. An exposed region of the tubular portion 206 that does not have the insulative coating may form the electrical contact 266. Alternatively, the electrical contact 266 may be a ring type electrode or other contact that is formed on the exterior of the tubular portion 206. The electrical contact 266 is configured to interface with a corresponding electrical contact (not shown) in the power supply 400 when the proximal end 202 of the delivery wire assembly 200 is inserted into the power supply 400. The electrical contact 266 of the second conductive path 264 is, of course, electrically isolated with respect to the electrical contact 216 of the first conductive path 262.

The power supply 400 depicted in FIG. 18 is similar to the one depicted in FIG. 1, however, it is configured for electrolytic (vs. thermal) detachment. Accordingly, in addition to the features of the power supply 400 depicted in FIG. 1, the power supply 400 depicted in FIG. 18 includes several alternative and additional features. The drive circuitry 402 typically operates by applying a substantially constant current (e.g., around 1.5 mA). The power supply 400 may include optional detection circuitry 420 that is configured to detect when the occlusive coil 300 has detached from the core wire 252. The detection circuitry 420 may identify detachment based upon a measured impedance value. A visual indicator 412 may indicate when the power supply 400 is being supplied to the current to the sacrificial electrolytic detachment zone 220. Another visual indicator 414 may indicate when the occlusive coil 300 has detached from the delivery wire 210. As an alternative to the visual indicator 414, an audible signal (e.g., beep) or even tactile signal (e.g., vibration or buzzer) may be triggered upon detachment. The detection circuitry 420 may be configured to disable the drive circuitry 402 upon sensing detachment of the occlusive coil 300.

The power supply 400 may also contain another visual indicator 416 that indicates to the operator when a legacy, non-bipolar delivery wire assembly is inserted into the power supply 400. As explained in the background above, prior devices used a separate return electrode that typically was in the form of a needle that was inserted into the groin area of the patient. The power supply 400 is configured to detect when one of the older non-bipolar delivery wire assemblies has been inserted. Under such situations, the visual indicator 416 (e.g., LED) is turned on and the user is advised to insert the separate return electrode (not shown in FIG. 1) into a port 418 located on the power supply 400.

Figure 22:
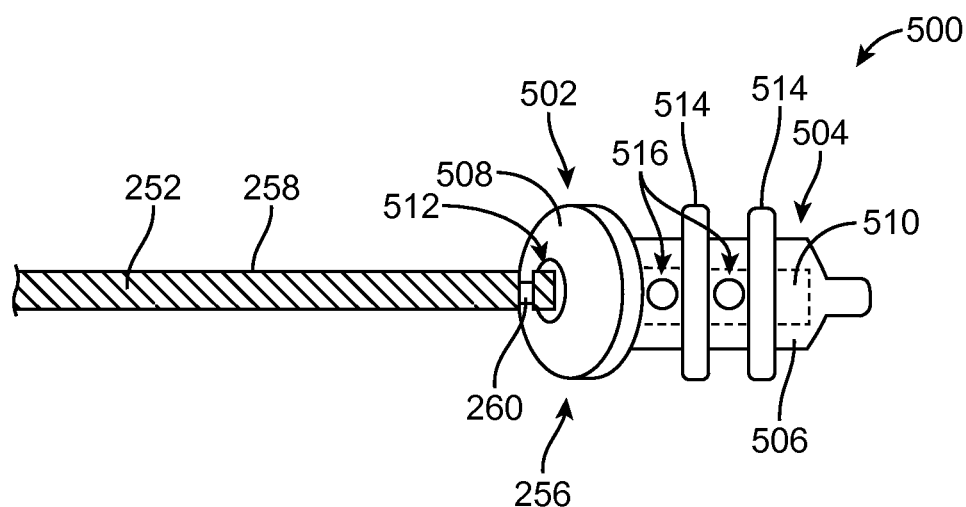
FIG. 22 is a detailed schematic view of a link with a core wire secured thereto, according to various embodiments of the disclosed inventions.
Figure 23:
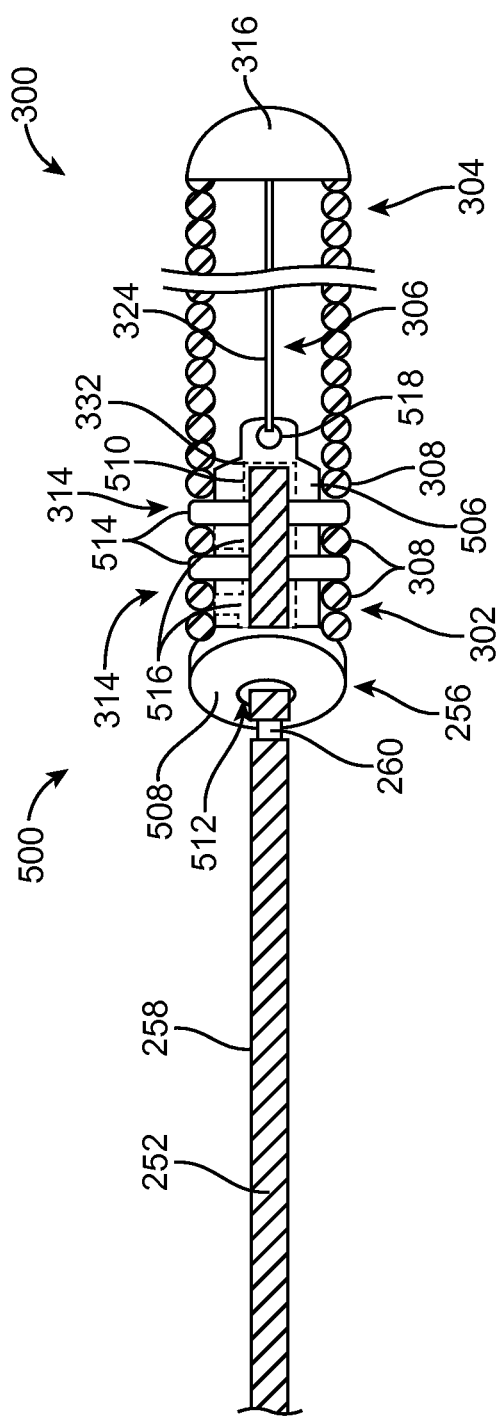

FIGS. 21-23 depict a link 500 secured to a vaso-occlusive coil 300 according to another embodiment of the disclosed inventions. The link 500 depicted in FIGS. 21-23 is similar to the one depicted in FIGS. 19-20, except that the link 500 defines two pairs of detents 514 instead of one. As shown in FIGS. 21 and 23, the two pairs of detents 514 interface with corresponding coil openings 314 formed by the open pitch of the proximal coil windings 308 to secure the link 500 to the vaso-occlusive coil 300. The link 500 designs described above improve assembly process learning curve, tack time, yield, and Cost of Goods.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A vaso-occlusive coil delivery assembly, comprising:
a pusher assembly defining a longitudinal axis;
an elongate tubular member having a proximal end portion attached to a distal end of the pusher assembly, the tubular member being aligned with the longitudinal axis of the pusher assembly and having a tubular member wall;
a vaso-occlusive coil defining an axial lumen and having first and second vaso-occlusive coil windings in a proximal end portion thereof, the first and second windings defining a vaso-occlusive coil opening therebetween, wherein a distal end portion of the tubular member wall extends into the axial lumen of the vaso-occlusive coil; and
a locking pin extending through the vaso-occlusive coil opening and through the distal end portion of the tubular member wall disposed in the axial lumen of the vaso-occlusive coil, thereby locking the tubular member to the vaso-occlusive coil,
wherein a central portion of the tubular member proximal of the locking pin is configured to be selectively severed from the proximal portion, so as to detach the vaso-occlusive coil from the pusher assembly.

2. The vaso-occlusive delivery assembly of claim 1, the tubular member defining an axial lumen, and further comprising a support coil disposed in the axial lumen of the tubular member, the support coil having first and second support coil windings defining a support coil opening therebetween, wherein the locking pin further extends through the support coil opening.

3. The vaso-occlusive delivery assembly of claim 2, wherein the support coil is secured to the tubular member.

4. The vaso-occlusive delivery assembly of claim 1, wherein the locking pin has an external portion that extends laterally outward of the vaso-occlusive coil opening, and is sized and shaped to prevent passage thereof through the vaso-occlusive coil opening.

5. The vaso-occlusive delivery assembly of claim 1, wherein the first and second vaso-occlusive coil windings is a first pair of windings, wherein the vaso-occlusive coil opening is a first vaso-occlusive coil opening, wherein the locking pin is a first locking pin, the vaso-occlusive delivery assembly further comprising:
   a second vaso-occlusive coil opening defined by a second pair of vaso-occlusive coil windings; and
   a second locking pin extending through the second vaso-occlusive coil opening and through the distal end portion of the tubular member wall disposed in the axial lumen of the vaso-occlusive coil, thereby further locking the tubular member to the vaso-occlusive coil.

6. The vaso-occlusive delivery assembly of claim 5, further comprising a locking pin connector disposed adjacent an exterior surface of the vaso-occlusive coil, wherein each of first and second locking pins has an external portion that extends laterally outward of respective first and second vaso-occlusive coil openings, and wherein the locking pin connector is attached to the respective external portions of the first and second locking pins.

7. The vaso-occlusive delivery assembly of claim 6, further comprising an adhesive that secures the first and second locking pins, and the locking pin connector, to the vaso-occlusive coil.

8. The vaso-occlusive delivery assembly of claim 5, wherein the first locking pin has an external portion comprising a hook that extends laterally outward of the first locking pin and through the distal end portion of the tubular member wall disposed in the axial lumen of the vaso-occlusive coil, thereby locking the tubular member to the vaso-occlusive coil opening, and wherein a distal end of the hook extends into the second locking pin and through the distal end portion of the tubular member wall disposed in the axial lumen of the vaso-occlusive coil, thereby locking the tubular member to the vaso-occlusive coil opening.

9. The vaso-occlusive delivery assembly of claim 1, wherein the central portion of the tubular member is configured to be thermally severed from the proximal portion.

10. The vaso-occlusive delivery assembly of claim 1, wherein the central portion of the tubular member is configured to be electrolytically severed from the proximal portion.

11. The vaso-occlusive delivery assembly of claim 1, wherein the tubular member wall is weakened to facilitate severing of the central portion from the proximal portion.

12. A vaso-occlusive delivery assembly, comprising:
a pusher assembly defining a longitudinal axis;
an elongate tubular member attached to, and extending distally from, a distal end of the pusher assembly, the tubular member being aligned with the longitudinal axis of the pusher assembly and having a tubular member wall;
a vaso-occlusive coil defining an axial lumen and having first and second vaso-occlusive coil windings in a proximal end portion thereof, the first and second windings defining a vaso-occlusive coil opening therebetween, wherein a distal end portion of the tubular member wall extends into the axial lumen of the vaso-occlusive coil;
a locking pin extending through the vaso-occlusive coil opening and through the distal end portion of the tubular member wall disposed in the axial lumen of the vaso-occlusive coil, thereby locking the tubular member to the vaso-occlusive coil; and
a stretch-resisting member disposed in the axial lumen of the vaso-occlusive coil, wherein a proximal end of the stretch-resisting member is coupled to the locking pin.

13. A vaso-occlusive delivery assembly, comprising:
a pusher assembly defining a longitudinal axis;
an elongate tubular member attached to, and extending distally from, a distal end of the pusher assembly, the tubular member being aligned with the longitudinal axis of the pusher assembly and having a tubular member wall;
a vaso-occlusive coil defining an axial lumen and having first and second vaso-occlusive coil windings in a proximal end portion thereof, the first and second windings defining a vaso-occlusive coil opening therebetween, wherein a distal end portion of the tubular member wall extends into the axial lumen of the vaso-occlusive coil;
a locking pin extending through the vaso-occlusive coil opening and through the distal end portion of the tubular member wall disposed in the axial lumen of the vaso-occlusive coil, thereby locking the tubular member to the vaso-occlusive coil; and
an adhesive securing the tubular member to the vaso-occlusive coil, wherein the adhesive is disposed within the axial lumen of the vaso-occlusive coil and within the vaso-occlusive coil opening between the first and second vaso-occlusive coil windings.

* * * * *